US012564193B2

(12) United States Patent
Tang et al.

(10) Patent No.: US 12,564,193 B2
(45) Date of Patent: Mar. 3, 2026

(54) ISOXAZOLINE-SUBSTITUTED BENZAMIDE DERIVATIVE, AND PREPARATION METHOD THEREFOR AND USE THEREOF

(71) Applicant: SHANDONG UNITED PESTICIDE INDUSTRY CO., LTD., Taian (CN)

(72) Inventors: Jianfeng Tang, Taian (CN); Huiwei Chi, Taian (CN); Jianting Wu, Taian (CN); Bin Yu, Taian (CN); Longxiang Xu, Taian (CN); Baoxiu Zhao, Taian (CN); Yi Yang, Taian (CN); Dongrong Li, Taian (CN)

(73) Assignee: SHANDONG UNITED PESTICIDE INDUSTRY CO., LTD., Taian (CN)

(*) Notice: Subject to any disclaimer, the term of this patent is extended or adjusted under 35 U.S.C. 154(b) by 488 days.

(21) Appl. No.: 18/003,454

(22) PCT Filed: Jul. 1, 2021

(86) PCT No.: PCT/CN2021/104101

§ 371 (c)(1),
(2) Date: Dec. 27, 2022

(87) PCT Pub. No.: WO2022/022221

PCT Pub. Date: Feb. 3, 2022

(65) Prior Publication Data

US 2023/0240298 A1 Aug. 3, 2023

(30) Foreign Application Priority Data

Jul. 30, 2020 (CN) ........................ 202010754471.7

(51) Int. Cl.

| | |
|---|---|
| ***C07D 413/12*** | (2006.01) |
| ***A01N 43/80*** | (2006.01) |
| ***A01P 7/02*** | (2006.01) |
| ***A01P 7/04*** | (2006.01) |

(52) U.S. Cl.

CPC ................ *A01N 43/80* (2013.01); *A01P 7/02* (2021.08); *A01P 7/04* (2021.08); *C07D 413/12* (2013.01)

(58) Field of Classification Search

CPC ......... C07D 413/12; A01N 43/80; A01P 7/02; A01P 7/04

See application file for complete search history.

(56) References Cited

U.S. PATENT DOCUMENTS

| | | | |
|---|---|---|---|
| 2,891,855 | A | 6/1959 | Hans et al. |
| 3,060,084 | A | 10/1962 | Littler |
| 3,235,361 | A | 2/1966 | Loux |
| 3,299,566 | A | 1/1967 | Macmullen |
| 3,309,192 | A | 3/1967 | Luckenbaugh |
| 3,920,442 | A | 11/1975 | Albert et al. |
| 4,144,050 | A | 3/1979 | Frensch et al. |
| 4,172,714 | A | 10/1979 | Albert |
| 5,180,587 | A | 1/1993 | Moore |
| 5,208,030 | A | 5/1993 | Hoy et al. |
| 5,232,701 | A | 8/1993 | Ogawa et al. |

FOREIGN PATENT DOCUMENTS

| | | | |
|---|---|---|---|
| CN | 101400662 | A | 4/2009 |
| CN | 101768129 | A | 7/2010 |
| CN | 102088856 | A | 6/2011 |
| CN | 102131789 | A | 7/2011 |
| CN | 111909143 | A | 11/2020 |
| DE | 3246493 | A1 | 6/1984 |
| GB | 2095558 | A | 10/1982 |
| WO | 9113546 | A1 | 9/1991 |
| WO | 2005085216 | A1 | 9/2005 |
| WO | 2009080250 | A2 | 7/2009 |
| WO | 2010027051 | A1 | 3/2010 |
| WO | 2011067272 | A1 | 6/2011 |
| WO | 2013078071 | A1 | 5/2013 |
| WO | 2020055955 | A1 | 3/2020 |

*Primary Examiner* — Brenda L Coleman

(74) *Attorney, Agent, or Firm* — NKL Law; Allen Xue

(57) ABSTRACT

An isoxazoline-substituted benzamide derivative, and a preparation method therefor and use thereof are provided. A compound represented by formula (I) or a salt thereof;

(I)

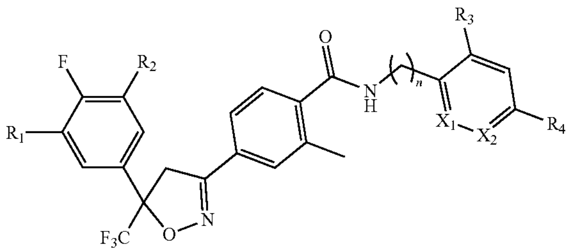

and the compound represented by formula (I) exhibits good activity against a variety of pests and mites in agriculture or other fields. Moreover, these compounds can achieve a good control effect at low doses, and can be used in preparation of pesticides and/or acaricides and have good application prospects.

10 Claims, No Drawings

ISOXAZOLINE-SUBSTITUTED BENZAMIDE DERIVATIVE, AND PREPARATION METHOD THEREFOR AND USE THEREOF

CROSS-REFERENCE TO RELATED APPLICATION

This application is a U.S. national stage entry of PCT International Application No. PCT/CN2021/104101, filed on Jul. 1, 2021, which claims the priority of Chinese Patent Application No. 202010754471.7 entitled "ISOXAZOLINE-SUBSTITUTED BENZAMIDE DERIVATIVE, AND PREPARATION METHOD THEREFOR AND USE THEREOF" and filed with China National Intellectual Property Administration on Jul. 30, 2020, the content of which is incorporated herein by reference in its entirety.

TECHNICAL FIELD

The present disclosure relates to the technical field of insecticides and acaricides, and in particular to an isoxazoline-substituted benzamide derivative, a preparation method therefor and use thereof.

BACKGROUND

The insecticides and acaricides play an extremely important role in solving the problem of human grain production for agricultural production increase. As the demand for safety of chemical substances and environmental impact increases day by day, development of safer pest control agents is desired. In addition, since pest control agents such as insecticides and acaricides are used for many years, the pests gradually develop resistance to these biological control agents, and thus the control effect is not satisfactory. Therefore, development of pest control agents having excellent safety, control effect, residual effect, and other properties is a trend in the future.

The Patent Document WO2005085216 discloses an isoxazoline compound $CK_1$ (Compound No. 5-241) shown below:

General formula

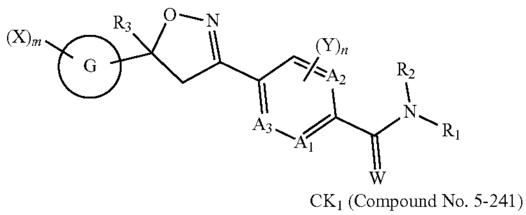

$CK_1$ (Compound No. 5-241)

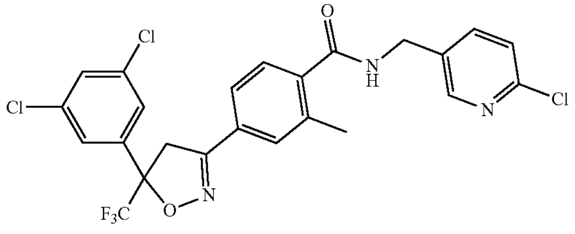

However, the biological activity of the compound described above is still to be further improved. The present inventors have conducted intensive studies to find an insecticide and acaricide having more excellent properties.

SUMMARY

To improve the problem described above, the present disclosure provides a compound of the following formula (I), or a stereoisomer, a racemate, a tautomer, a nitrogen oxide or a pharmaceutically acceptable salt thereof, (I)

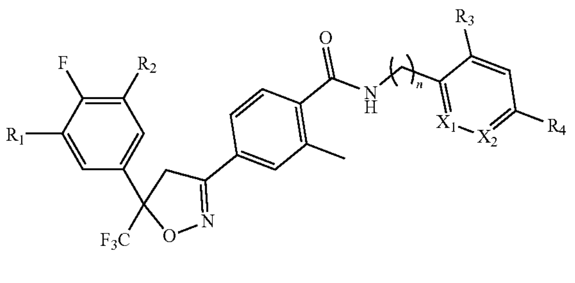

$R_1$ and $R_2$ are identical or different and are each independently selected from F and Cl;

$R_3$ and $R_4$ are identical or different and are each independently selected from H, Cl and $CF_3$, and $R_3$ and $R_4$ are not both H;

$X_1$ and $X_2$ are each independently selected from CH and N, and $X_1$ and $X_2$ are not both CH or N;

n is selected from 1 and 2;

according to an embodiment of the present disclosure, in formula (I), $X_1$ is CH, and $X_2$ is N;

$R_1$ and $R_2$ are identical or different and are each independently selected from F and Cl;

$R_3$ and $R_4$ are identical or different and are each independently selected from H, Cl and $CF_3$, and $R_3$ and $R_4$ are not both H;

n is selected from 1 and 2.

according to an embodiment of the present disclosure, in formula (I), $X_1$ is N, and $X_2$ is CH;

$R_1$ and $R_2$ are identical or different and are each independently selected from F and Cl;

$R_3$ and $R_4$ are identical or different and are each independently selected from Cl and $CF_3$, and $R_3$ and $R_4$ are not both H;

n is selected from 1 and 2.

As an example, the compound of formula (I) is selected from the following compounds,

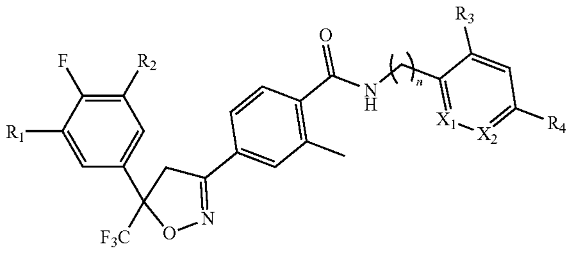

TABLE 1

| No. | $X_1$ | $X_2$ | $R_1$ | $R_2$ | $R_3$ | $R_4$ | n |
|---|---|---|---|---|---|---|---|
| 1. | CH | N | Cl | Cl | H | Cl | 1 |
| 2. | CH | N | F | F | H | Cl | 1 |
| 3. | CH | N | Cl | Cl | $CF_3$ | H | 1 |
| 4. | CH | N | F | F | $CF_3$ | H | 1 |
| 5. | CH | N | Cl | Cl | $CF_3$ | Cl | 1 |
| 6. | CH | N | F | F | $CF_3$ | Cl | 1 |
| 7. | CH | N | Cl | Cl | Cl | Cl | 1 |
| 8. | CH | N | F | F | Cl | Cl | 1 |
| 9. | N | CH | Cl | Cl | Cl | $CF_3$ | 1 |
| 10. | N | CH | F | F | Cl | $CF_3$ | 1 |
| 11. | N | CH | Cl | Cl | Cl | Cl | 1 |
| 12. | N | CH | F | F | Cl | Cl | 1 |
| 13. | N | CH | Cl | Cl | Cl | H | 1 |
| 14. | N | CH | F | F | Cl | H | 1 |
| 15. | CH | N | Cl | Cl | H | Cl | 2 |
| 16. | CH | N | F | F | H | Cl | 2 |
| 17. | CH | N | Cl | Cl | $CF_3$ | H | 2 |
| 18. | CH | N | F | F | $CF_3$ | H | 2 |
| 19. | N | CH | Cl | Cl | Cl | $CF_3$ | 2 |
| 20. | N | CH | F | F | Cl | $CF_3$ | 2 |

The present disclosure also provides a preparation method for the compound of formula (I) described above, which comprises the following step A) or step B):

step A), subjecting a compound of formula (II) and a compound of formula (III) to a condensation reaction to give the compound of formula (I); or

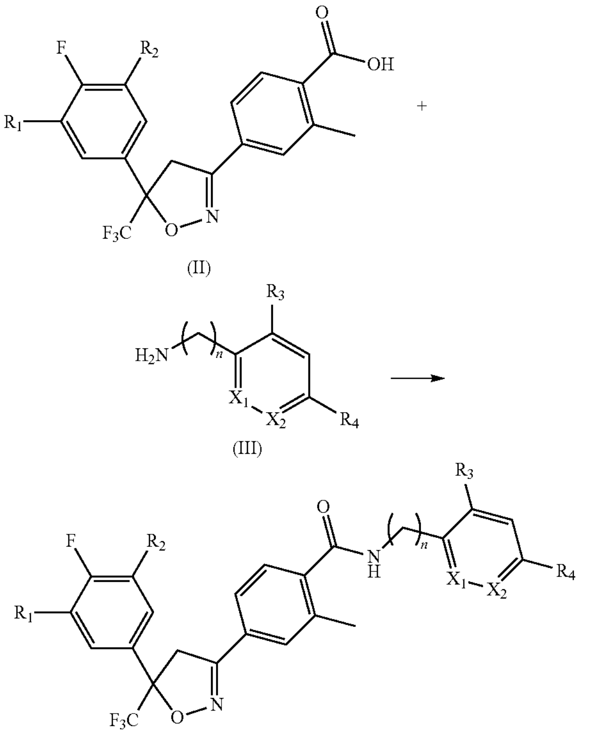

(II) (III) (I)

step B),

B1), reacting the compound of formula (II) with a halogenating agent to give a compound of formula (IV); and B2), reacting the compound of formula (IV) with the compound of formula (III) to give the compound of formula (I);

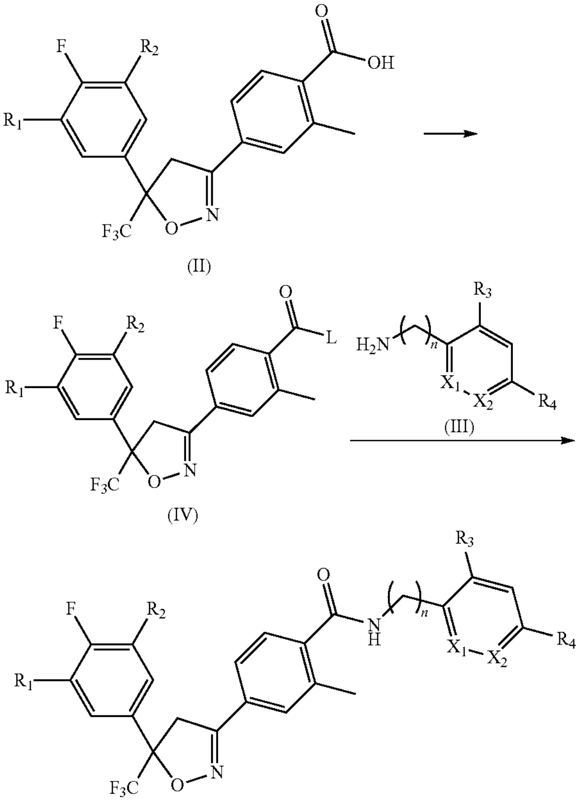

(II) (IV) (III) (I)

wherein $R_1$, $R_2$, $R_3$, $R_4$, $X_1$, $X_2$ and n are defined as above; L is selected from a leaving group, such as Cl, Br, I or F.

The amines of formula (III) may be prepared by using methods described in WO2009080250 or may be prepared by using methods known to those skilled in the art.

According to an embodiment of the present disclosure, the reaction in step A) may be performed in the presence of a condensing agent selected from at least one of N,N-dicyclohexylcarbodiimide (DCC), N,N-dii sopropylcarbodiimide (DIC), 1-hydroxybenzotriazole (HOBT), 2-(7-azabenzotriazole)-N,N,N,N-tetramethyluronium hexafluorophosphate (HATU) and benzotriazol-1-yl-oxytripyrrolidino-phosphonium hexafluorophosphate (PyBOP);

according to an embodiment of the present disclosure, the reaction in step A) may be performed in the presence of a base which may be an inorganic base, for example, selected from at least one of pyridine, triethylamine, 4-(dimethylamino)pyridine (DMAP) and diisopropylethylamine (DIEA);

according to an embodiment of the present disclosure, the reaction in step A) is performed in a solvent selected from at least one of N,N-dimethylacetamide, N,N-dimethylformamide, tetrahydrofuran, 2-methyltetrahydrofuran, dioxane, acetonitrile, toluene, dichloromethane and 1,2-dichloroethane;

according to an embodiment of the present disclosure, the reaction temperature in step A) may be −5° C. to 120° C., e.g., 0° C. to 50° C., such as 15° C. to 30° C.

According to an embodiment of the present disclosure, the halogenating agent in step B1) is selected from thionyl chloride, oxalyl chloride and thionyl chloride;

according to an embodiment of the present disclosure, the reaction temperature in step B1) may be 0° C. to 100° C., e.g., 0° C. to 50° C., such as 0° C. to 30° C.;

according to an embodiment of the present disclosure, the reaction in step B2) may be performed in the presence of a base which may be selected from one, two or more of organic and inorganic bases, such as pyridine, triethylamine, 4-(dimethylamino)pyridine (DMAP), diisopropylethylamine (DIEA), sodium carbonate, potassium carbonate, sodium hydroxide, potassium hydroxide, potassium tert-butoxide, sodium hydride and the like. The solvent may preferably be N,N-dimethylacetamide, N,N-dimethylformamide, dioxane, toluene, dichloromethane or 1,2-dichloroethane;

according to an embodiment of the present disclosure, the reaction temperature in step B2) may be 0° C. to 120° C., e.g., 0° C. to 50° C., such as 15° C. to 30° C.

According to an embodiment of the present disclosure, the preparation method for the compound of formula (II) comprises the following steps:

according to an embodiment of the present disclosure, step (1) may be performed in the presence of a base selected from an organic base such as triethylamine, sodium acetate, and an inorganic base such as sodium bicarbonate; the reaction solvent is selected from an alcohol solvent such as methanol, ethanol and the like, water and a mixture thereof; the reaction temperature may be 0° C. to 100° C., preferably 15° C. to 30° C.

According to an embodiment of the present disclosure, step (2) may be performed in the presence of a catalyst selected from tetrakis(triphenylphosphine)palladium, palladium acetate and bis(triphenylphosphine)palladium chloride;

according to an embodiment of the present disclosure, step (2) may be performed in the presence of a base selected from sodium carbonate, potassium carbonate, pyridine, triethylamine and 4-(dimethylamino)pyridine; the solvent is selected from toluene, tetrahydrofuran, N,N-dimethylformamide and water; the reaction temperature may be 30° C. to 150° C., e.g., 50° C. to 120° C.

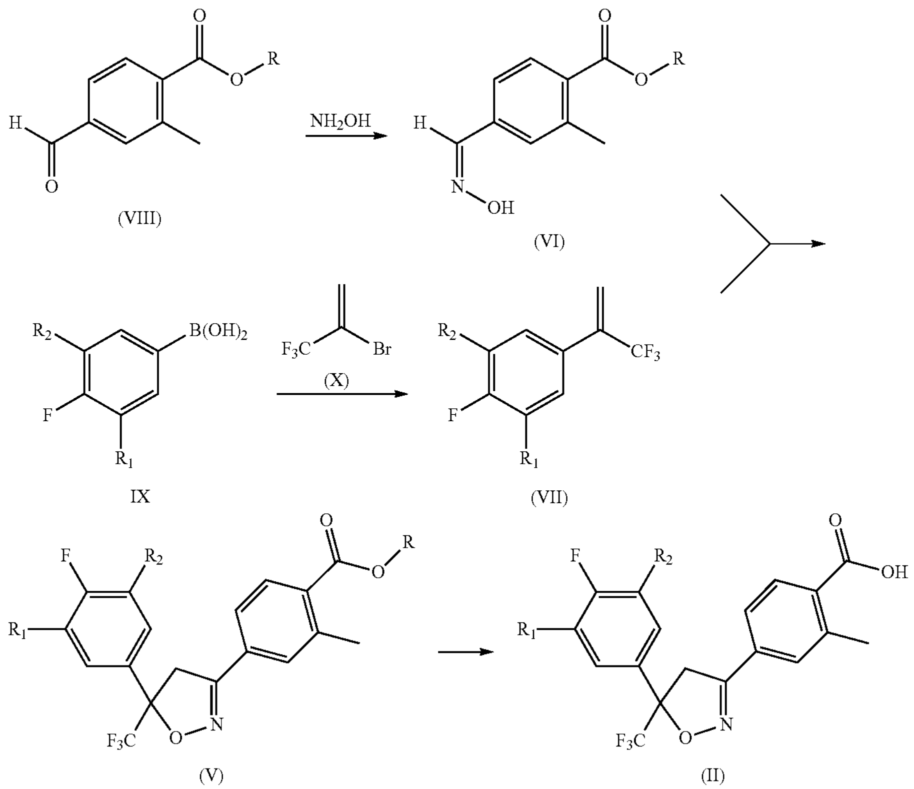

(VIII) (VI) IX (VII) (V) (II)

(1) reacting a compound of formula (VIII) with hydroxylamine or hydroxylamine hydrochloride to give a compound of formula (VI);

(2) reacting a compound of formula (IX) with a compound of formula (X) to give a compound of formula (VII);

(3) reacting the compound of formula (VI) with the compound of formula (VII) to give a compound of formula (V); and (4) hydrolyzing the compound of formula (V) to give the compound of formula (II);

wherein $R_1$, $R_2$, $R_3$, $R_4$, $X_1$, $X_2$ and n are defined as above; R is an alkyl group containing 1 to 6 carbon atoms, such as methyl, ethyl, propyl, isopropyl or tert-butyl;

According to an embodiment of the present disclosure, step (3) may be performed in the presence of a halogenating agent which may be N-chlorosuccinimide (NCS) or N-bromosuccinimide (NBS); the reaction temperature may be 0° C. to 100° C., e.g., 15° C. to 30° C.

According to an embodiment of the present disclosure, step (3) may be performed in the presence of a base selected from at least one of triethylamine, pyridine, sodium bicarbonate and sodium carbonate; the reaction temperature may be 0° C. to 100° C., e.g., 15° C. to 30° C.

According to an embodiment of the present disclosure, step (4) may be performed in the presence of a base selected from at least one of sodium hydroxide, potassium hydroxide and lithium hydroxide, or may be treated with an acid such as trifluoroacetic acid in dichloromethane.

According to an embodiment of the present disclosure, the reaction temperature in step (4) may be 0° C. to 150° C., e.g., 15° C. to 80° C.

The aldehyde of formula (VIII) may be commercially available or prepared by using methods known to those skilled in the art.

The boronic acid of formula (IX) and the ethenyl compound of formula (X) may be commercially available or prepared by using methods known to those skilled in the art.

According to an embodiment of the present disclosure, the reaction may be performed with reference to the method described in Patent Document WO2009080250.

For the preparation of the compound of formula (I) and a starting material thereof, suitable reaction conditions and starting materials may be selected according to different situations. For example, only one substituent may be substituted with another substituent according to the present disclosure in a one-step reaction, or multiple substituents may be substituted with other substituents according to the present disclosure in the same reaction step.

If the compounds may not be obtained via the routes described above, they may be prepared by deriving other compounds or by conventionally changing the synthetic routes.

The reaction mixture is post-treated by following conventional methods, such as purifying the crude product by mixing with water, phase separation and suitably chromatography, for example, on alumina or silica gel.

The pharmaceutically acceptable salt of the compound of formula (I) of the present disclosure may be prepared by using known methods. For example, an acid addition salt of the compound of formula (I) is obtained through suitable acid treatment. The preparation method therefor is as follows: the pharmaceutically acceptable salt of the compound of formula (I) may be conveniently obtained by reacting the compound of formula (I) with an acid such as hydrochloric acid, sulphuric acid, phosphoric acid, acetic acid, trifluoroacetic acid, malic acid, citric acid or the like in a solvent such as water, diethyl ether or toluene.

An isomer mixture of the compound of formula (I) may be obtained by using the preparation method described above, and if a pure isomer is desired, the separation may be performed by a conventional method such as crystallization or chromatography.

All reactions described above may readily be performed at atmospheric pressure or the own pressure of a particular reaction, unless otherwise indicated.

The present disclosure also provides a pesticidal composition, such as an insecticidal and/or acaricidal composition, comprising one, two or more of the compound of formula (I), or the stereoisomer, the racemate, the tautomer, the nitrogen oxide or the pharmaceutically acceptable salt thereof as an active ingredient.

According to an embodiment of the present disclosure, the active ingredient is present in the composition in an amount of 0.1 wt % to 99.9 wt %, such as 0.5 wt % to 99 wt %.

According to an embodiment of the present disclosure, one, two or more agriculturally and/or forestry and/or hygienically acceptable carriers are also included in the composition.

According to an embodiment of the present disclosure, the composition may be administered in the form of a preparation.

For example, the compound of formula (I) as an active ingredient is dissolved or dispersed in a carrier or formulated into a preparation so as to be more easily dispersible for insecticidal and/or acaricidal use.

According to an embodiment of the present disclosure, the preparation includes, but is not limited to, the following forms: wettable powder, oil suspension, water suspension, aqueous emulsion, aqueous solution, emulsifiable concentrate, microcapsule or the like.

According to an embodiment of the present disclosure, a liquid or solid carrier, and optionally a surfactant, may also be added to the composition.

The present disclosure also provides use of the one, two or more of the compound of formula (I), or the stereoisomer, the racemate, the tautomer, the nitrogen oxide or the pharmaceutically acceptable salt thereof as a pesticide, such as an insecticide and/or an acaricide.

The present disclosure also provides use of the one, two or more of the compound of formula (I), or the stereoisomer, the racemate, the tautomer, the nitrogen oxide or the pharmaceutically acceptable salt thereof for the manufacturing of a pesticide, such as an insecticide and/or an acaricide.

The present disclosure also provides a method for controlling pests and/or mites, which comprises applying an effective amount of one, two or more of the compound of formula (I), or the stereoisomer, the racemate, the tautomer, the nitrogen oxide or the pharmaceutically acceptable salt thereof, or applying the composition to a growth medium of pests and/or mites.

According to an embodiment of the present disclosure, the effective amount is 10 grams to 1000 grams per hectare, preferably 20 grams to 500 grams per hectare.

The active substances according to the present disclosure or the active substances to be used in the present disclosure are suitable, in view of good plant tolerance, advantageous warm-blooded animal toxicity and good environmental compatibility, for protecting plants and plant organs, increasing harvest yields, improving the quality of the harvest and for controlling pests, mites and the like which occur, in particular, in agriculture, horticulture, animal husbandry, forestry, gardens and leisure facilities, in warehouse pest protection and material protection, and in the hygiene sector. They are preferably used as plant protection compositions. They are active against conventional sensitive and resistant species and against all or individual developmental stages. The pests and mites described above include, but are not limited to:

*arthropoda*, in particular Arachnida, for example, *Acarus* spp., *Aceriasheldoni, Aculops* spp., *Aculus* spp., *Amblyomma* spp., *Amphitetranychus viennensis, Argas* spp., *Boophilus* spp., *Brevipalpus* spp., *Bryobiagraminum, Bryobiapraetiosa, Centruroides* spp., *Chorioptes* spp., *Dermanyssus gallinae, Dermatophagoides pteronyssinus, Dermatophagoides farinae, Dermacentor* spp., *Eotetranychus* spp., *Epitrimerus pyri, Eutetranychus* spp., *Eriophyes* spp., *Glycyphagus domesticus, Halotydeus destructor, Hemitarsonemus* spp., *Hyalomma* spp., *Ixodes* spp., *Latrodectus* spp., *Loxosceles* spp., *Metatetranychus* spp., *Neutrombicula autumnalis, Nuphersa* spp., *Oligonychus* spp., *Ornithodorus* spp., *Ornithonyssus* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpiomaurus, Steneotarsonemus* spp., *Steneotarsonemus spinki, Tarsonemus* spp., *Tetranychus* spp., *Trombicula alfreddugesi, Vaejovis* spp., and *Vasates lycopersici;*

Coleoptera (beetle): *Acanthoscelides* spp. (*Curculio*), *Acanthoscelides obtectus* (*Bruchus pisorum*), *Agrilus planipennis* (*Agrilus marcopoli* Obenberger), *Agriotes* spp. (wireworm), *Anoplophora glabripennis* (Asian longhorned beetle), *Anthonomus* spp. (Curculionidae), *Anthonomus grandis* (cotton bollworm), *Aphidius* spp., *Apion* spp. (*Curculio*), *Apogonia* spp. (grub), *Atacnius sprctulus* (velvety chafer), *Atomaria linearis* (pygmy mangold beetle), *Aulacophore* spp., *Bothynoderes punctiventris* (*Bothynoderes punctiremtris* Germar), *Bruchus* spp. (*Curculio*), *Bruchus pisorum* (*Bruchus pisorum*), *Cacoesia* spp., *Callosobruchus maculatus* (peaweevil), *Carpophilus hemipteras* (*Carpophllus hemipt-prus*), *Cassida vittata, Ccrostcrna* spp., *Ccrotoma* spp. (Chrysomcids), *Cerotoma trifurcata, Ceutorhynchus* spp., *Ceutorhynchus assimilis* (cabbage seedpod weevil), *Ceutorhynchus napi* (cabbage *Curculio*), *Chaetocnema* spp. (*Zlatna trichomonijaza*), *Colaspis* spp. (*Eupolyphaga*), *Conoderus scalaris, Conoderus stigmosus, Conotrachelus nenuphar* (*Conotrachelus nenuphar* Herbst), *Cotinus nitidis* (Green June beetle), *Crioceris asparagi* (*Crioceris asparagi*), *Cryptolestes ferrugincus* (rusty grainbeetle), *Cryptolestes pusillus* (flat grain beetle), *Cryptolestes turcicus* (Turkish grainbeetle), *Ctenicera* spp. (nematode), *Curculio* spp. (*Curculio*), *Cyclocephala* spp. (grub), *Cylindrocpturus adspersus* (sunflower stem weevil), *Deporaus marginatus* (mango leaf-cutting weevil), *Dermestes lardarius, Dermestes maculates, Diabrotica* spp. (leaf beetle), *Epilachna varivcstis, raustinuscubae, Hylobius pales* (*pales* weevil), *Hypera* spp. (*Curculio*), *Hypera postica* (*Hypera postica*), *Hyperdoes* spp. (*Hyperodes* weevil), *Hypothenemus hampei* (coffee berry borer), *Ips* spp. (engravers), *Lasioderma serricorne* (tobacco beetle), *Leptinotarsa decemlinea* to (Colorado potato beetle), *Liogenys fuscus, Liogenys suturalis, Lissorhoptrus oryzophilus, Lyctus* spp., (powder post beetles), *Maecolaspis joliveti, Megascelis* spp., *Melanotus communis, Meligethes* spp., *Meligethes aeneus* (blossom beetle), *Melolontha melolontha, Oberea brevis, Oberea linearis, Oryctes rhinoceros* (date palm beetle), *Oryzaephilus mercator* (merchant grain beetle), *Oryzaephilus surinamensis* (sawtoothed grain beetle), *Otiorhynchus* spp. (*Curculio*), *Oulemamelanopus* (cereal leaf beetle), *Oulema oryzae, Pantomorus* spp. (*Curculio*), *Phyllophaga* spp. (May-June Beetle), *Phyllophaga cuyabana, Phyllotreta* spp. (chrysomonad), *Phynchites* spp., *Popillia japonica* (Japanese beetle), *Prostephanus truncates* (larger grain borer), *Rhizopertha dominica* (lesser grain borer), *Rhizotrogus* spp. (European chafer), *Rhynchophorus* spp. (*Curculio*), *Scolytus* spp. (Cossidae), *Shenophorus* spp. (Granary weevil), *Sitonalincatus* (pea leaf weevil), *Sitophilus* spp. (grain weevil), *Sitophilus* granaries (granary weevil), *Sitophilus oryzae* (rice weevil), *Stegobiumpaniceum* (drugstore beetle), *Tribolium* spp. (flour beetle), *Tribolium castaneum* (red flour beetle), *Tribolium confusum* (confused flour beetle), *Trogoderma variabile* (warehouse beetle) and *Zabrustene bioides;*

*Dermaptcra* (earwig);

*Dictyoptera* (cockroach): *Blattella germanica* (German cockroach), *Blatta orientalis* (oriental cockroach), *Parcoblatta pennylvanica, Periplaneta americana* (American cockroach), *Periplaneta australoasiae* (Australian cockroach), *Pcriplancta brunnca* (brown cockroach), *Periplaneta fuliginosa* (smoky brown cockroach), *Pyncoselus suninamensis* (Surinam cockroach) and *Supella longipalpa* (brown banded cockroach);

*Diptera* (housefly): *Aedes* spp. (mosquito), *Agromyza frontella* (alfalfa blotch leafminer), *Agromyza* spp. (fly), *Anastrepha* spp. (fruit fly), *Anastrepha suspensa* (Caribbean fruit fly), *Anopheles* spp. (mosquito), *Batrocera* spp. (fruit fly), *Bactrocera cucurbitae* (Melon fly), *Bactrocera dorsalis* (oriental fruit fly), *Ceratitis* spp. (fruit fly), *Ceratitis capitata* (Mediterranean fruit fly), *Chrysops* spp. (Deerfly), *Cochliomyia* spp. (Screwworm), *Contarinia* spp. (*Diarthronomyia chrysanthemi* Ahlberg), *Culex* spp. (Mosquitoes), *Dasineura* spp. (*Diarthronomyia chrysanthemi* Ahlberg), *Dasineura brassicae, Delia* spp., *Delia platura* (seed corn maggot), *Drosophila* spp. (vinegar fly), *Fannia* spp. (Muscid fly), *Fannia canicularis* (little house fly), *Fannia scalaris* (*Fannia* scalaris), *Gasterophilus intestinalis* (*Gastrophilus intestinalis*), *Gracillia perseae, Haematobia irritans* (horn fly), *Hylemyia* spp. (root maggot), *Hypoderma lineatum* (common cattle grub), *Liriomyza* spp. (fly), *Liriomyza brassica* (serpentine leafminer), *Melophagus ovinus* (sheep tick), *Musca* spp. (Muscid fly), *Musca autumnalis* (face fly), *Vusca domestica* (house fly), *Oestrus ovis* (sheep bot fly), *Oscinella frit* (wheat black bulb-worm), *Pegomyia betae* (beetle afminer), *Phorbia* spp., Psilarosae (carrot rust fly), *Rhagoletis cerasi* (cherry fruit fly), *Rhagoletis pomonella* (apple maggot), *Sitodiplosis mosellana* (orange wheat blossom midge), *Stomoxys calcitruns* (stable fly), *Tahanus* spp. (horse fly) and *Tipula* spp. (crane fly);

*hemiptera* (stinkbug): *Acrosternum hilare* (green stink bug), *Blissus leucopterus* (chinch bug), *Calocoris norvegicus* (potato mirid), *Cimex hemipterus* (tropical bed bug), *Cimex lectularius* (bed hug), *Daghertus fasciatus, Dichelops furcatus, Dysdercus suturellus* (cotton stainer), *Edessa meditabunda, Eurygaster maura* (cereal bug), *Euschistus heros, Euschistus servus* (brown stink bug), *Helopeltis antonii, Helopeltis theivora* (tea blight plant bug), *Lagynotomus* spp. (Stinkbug), *Leptocorisa oratorius, Leptocorisa varicornis, Lygus* spp. (plant bug), *Lygus hesperus* (western tarnished plant bug), *Maconellicoccus hirsutus, Neurocolpus longirostris, Nezara viridula* (southern green stink bug), *Phytocoris* spp. (leaf bug), *Phytocoris californicus, Phytocoris relativus, Piezodorus guildingi, Poecilocapsus lineatus* (four lined plant bug), *Psallus vaccinicola, Pseudacysta perseae, Scaptocoris castanea* and *Triatoma* spp. (bloodsucking conenose bug/kissing bug);

*homoptera* (aphid, scale, whitefly, leafhopper): Acrythosiphon pisum (pea aphid), *Adelges* spp. (*Adelges*), *Aleurodes proletella, Aleurodicus disperses, Aleurothrixus flccosus* (woolly whitefly), *Aluacaspis* spp., *Amrasca bigutella bigutella, Aphrophora* spp. (leafhopper), *Aonidiella aurantii* (California red scale), *Aphis* spp. (Aphid), *Aphis gossypii* (cotton aphid), *Aphis pomi* (apple aphid), *Aulacorthitm solani* (foxglove aphid), *Bemisia* spp. (whitefly), *Bemisia argentifolii, Bemisia tabaci* (sweet potato whitefly), *Bemisia tabaci* (Gennadius), *Brachycolus noxius* (Russian aphid), *Brachycorynclia asparagi* (asparagus aphid), *Brevennia rehi, Brevicoryne brassicae, Ceroplastes* spp. (Scale), *Ceroplastes rubens* (red wax scale), *Chionaspis* spp. (scale), *Chrysomphalus* spp. (scale), *Coccus* spp. (scale), *Dysaphis plantaginea* (rosy apple aphid), *Empoasca* spp. (leafhopper), *Eriosoma lanigerum* (woolly apple aphid), *Icerya purchasi* (cottony cushion scale), *Idioscopus nitidulus* (mango leafhopper), *Laodelphax striatellus* (smaller brown planthopper), *Lepidosaphes* spp., *Macrosiphum* spp., *Macrosiphum euphorbiae* (potato aphid), *Macrosiphum granarium* (English grain aphid), *Macrosiphum rosae* (rose aphid), *Macrosteles quadrilineatus* (aster leaf hopper), *Mahanarva frimbiolata, Metopolophium dirhodum* (rose grain aphid), *Midis longicornis, Myzus persicae* (green peach aphid), *Nephotettix* spp. (leafhopper), *Nephotettix cinctipes* (green leafhopper), *Nilaparvata lugens* (brown planthopper), *Parlatoria pergandii* (chaff scale), *Parlatoria ziziphi* (ebony scale), *Peregrinus maidis* (corn delphacid), *Philaenus* spp. (spittle bug), *Phylloxera vitifoliae* (grape *phylloxera*), *Physokermes piceae* (spruce bud scale), *Planococcus* spp. (mealy bug), *Pseudococcus* spp. (mealy bug), *Pscudococcus brcvipcs* (pincapplemcaly bug), *Quadraspidiotus perniciosus* (San Jose scale), *Rhapalosiphum* spp. (aphid), *Rhapalosiphum maida* (corn leaf aphid), *Rhapalosiphum padi* (oat bird-cherry aphid), *Saissetia* spp. (scale), *Saissetia oleae* (*Parlatoria zizyphus* (Lucas)), *Schizaphis graminum* (greenbug), *Sitobion avenge* (English grain aphid), *Sogatella furcifera* (white-backed planthopper), *Therioaphis* spp. (Aphid), *Toumeyella* spp. (scale), *Toxoptera* spp. (Aphid), *Trialeurodes* spp. (Whitefly), *Trialeurodes vaporariorum* (greenhouse whitefly), *Trialeurodes abutiloneus* (banded wing whitefly), *Unaspis* spp. (scale), *Unaspis yanonensis* (arrowhead scale) and *Zulia entreriana;*

*hymenoptera* (ant, wasp and bee): *Acromyrrmex* spp., *Athaliarosae, Atta* spp. (Leaf cutting ants), *Camponotus* spp. (carpenter ant), *Diprion* spp. (saw fly), *Formica* spp. (Ant), *Iridomyrmex humilis* (Argentine ant), *Monomorium* spp., *Monomorium minumum* (little black ant), *Monomorium pharaonis* (Pharaoh ant), *Neodiprion* spp. (Sawfly), *Pogonomyrmex* spp. (harvester ant), *Polistes* spp. (paper wasp), *Solenopsis* spp. (fire ant), *Tapoinoma sessile* (odorous house ant), *Tetranomorium* spp. (pavement ant), *Vespula* spp. (yellow jacket) and *Xylocopa* spp. (carpenter bee);

Isoptera (termite): *Coptotermes* spp., *Coptotermes curvignathus, Coptotermes frenchii, Coptotermes formosanus* (Formosan subterranean termite), *Cornitermes* spp. (nasute termite), *Cryptotermes* spp. (dry-wood termite), *Heterotermes* spp. desert subterranean termite), *Heterotermes aureus, Kalotermes* spp. (dry-wood termite), *Incistitermes* spp. (dry-wood termite), *Macrotermes* spp. (fungus growing termite), *Marginitermes* spp. (dry-wood termite), *Microcerotermes* spp. (harvester termite), *Microtermesobesi, Procornitermes* spp., *Reticulitermes* spp. (subterranean termite), *Reticulitermes banyulensis, Reticulitermes grassei, Reticulitermes flavipes*) (Eastern subterranean termite), *Reticulitermes hageni, Reticulitermes hesperus* (Western subterranean termite), *Reticulitermes santonensis, Reticulitermes speratus, Reticulitermes tibialis, Reticulitermes virginicus, Schedorhinotermes* spp. and *Zootermopsis* spp. (damp wood termite);

*lepidoptera* (moth and butterfly): *Achoeajanata, Adoxophyes* spp., *Adoxophyesorana, Agrotis* spp. (cutworm), *Agrotis ipsilon* (black cutworm), *Alabama argillacea* (cotton leaf worm), *Amorbia cuneana, Amyelosi transitella* (navel orange worm), *Anacamptodes defectaria, Anarsia lineatella* (peach twig borer), *Anomissa bulijera* (jute looper), *Anticarsia gemmatalis* (velvetbean caterpillar, *Archipsar gyrospila* (fruit tree leafroller), *Archips rosana* (rose leafroller), *Argyrotaenia* spp. (tortricid moth), *Argyrotaenia citrana* (orange *tortrix*), *Autographa gamma, Bonagota cranaodcs, Borbo cinnara* (rice leaffolder), *Buccula trixthurberiella* (cotton leaf perforator), *Caloptilia* spp. (Leafminer), *Capua reticulana, Carposina niponensis* (peach fruit moth), *Chilo* spp., *Chlumetia transversa* (mango shoot borer), *Choristoneura rosaceana* (oblique banded leaf roller), *Chrysodeixis* spp., *Cnaphalocerus medinalis* (grass leafroller), *Colias* spp., *Conpomorpha cramerella, Cossus* (Cossidae), *Crambus* spp. (Sod webworm), *Cydia funebrana* (plum fruit moth), *Cydia molesta* (oriental fruit moth), *Cydia nignicana* (pea moth), *Cydia pomonella* (codling moth), *Darnadiducta, Diaphania* spp. (stem borer), *Diatraea* spp. (stalk borer), *Diatraea saccharalis* (sugarcane borer), *Diatraea grandiosella* (southwester cornborer), *Earias* spp. (*Helicoverpa armigera*), *Earias insulata* (Egyptian bollworm), *Earias* vit. *ella* (rough northern bollworm), *Ecdytopopha aurantianum, Elasmopalpus lignosellus* (lesser cornstalk borer), *Epiphysia spostruttana* (light brown apple moth), *Ephestia* spp. (false meal moth), *Ephestia cautella* (almond moth), *Ephestia elutella* (tobbaco moth), *Ephestia kuehniella* (Mediterranean flour moth), *Epimeces* spp., *Epinotia aporema, Erionota thrax* (banana skipper), *Eupoecilia ambiguella* (grape berry moth), *Euxoa auxiliaris* (army cutworm), *Feltia* spp. (cutworm), *Gortyna* spp. (stem borer), *Grapholita molesta* (oriental fruit moth), *Hedylepta indicata* (bean leaf webber), *Helicoverpa* spp. (noctuid), *Helicoverpa armigera* (cotton bollworm), *Helicoverpa zea* (*Ostrinia nubilalis* (eumenid poher wasp/*Helicoverpa armigera*)), *Heliothis* spp. (noctuid), *Heliothis virescens* (tobacco budworm), *Hellula undalis* (cabbageweb worm), *Indarbela* spp. (root borer), *Keiferia lycopersicella* (tomato pinworm), *Leucinodes orbonalis* (eggplant fruit borer), *Leucoptera malifoliella, Lithocollectis* spp., *Lobesia botrana* (grape fruit moth), *Loxagrotis* spp. (noctuid), *Loxagrotis albicosta* (Western bean cutworm), *Lymantria dispar* (gypsy moth), *Lyonetia clerkella* (apple leafminer), *Mahasena corbetti* (oil palm bagworm), *Malacosoma* spp. (tent caterpillars), *Mamestra brassicae* (cabbage armyworm), *Maruca testulalis* (*Maruca testulalis* Geyer), *Metisa plana* (bagworm), *Mythimna unipuncta* (true armyworm), *Neoleucinodes elegantalis* (small tomato borer), *Nymphula depunctalis* (ricecaseworm), *Operophthera brumata* (winter moth), *Ostrinia nubilalis* (European corn borer), *Oxydia vesulia, Pandemis cerasana* (common currant *tortrix*), *Pandemis heparana* (brown apple *tortrix*), *Papilio demodocus, Pectinophora gossypiella* (pink bollworm), *Peridroma* spp. (cutworm), *Peridroma saucia* (variegated cutworm), *Perileucoptera coffeella* (white coffee leafminer), *Phthorimaea operculella* (potato tuber moth), *Phyllocnisitis citrella, Phyllonorycter* spp. (leafminer), *Pieris rapae* (imported cabbageworm), *Plathypena scabra, Plodia interpunctella* (Indian meal moth), *Plutella xylostella* (diamondback moth), *Polychrosis viteana* (grape berry moth), *Prays endocarps, Prays zoleae* (olive moth), *Pseudaletia* spp. (noctuid), *Pseudaletia unipunctata* (army worm), *Pseudoplusia includens* (soybean looper), *Rachiplusia nu, Chilo suppressalis, Scirpophaga incertulas, Sesamia* spp. (stem borer), *Sesamia inferens* (pink rice stemborer), *Sesamia nonagrioides, Setora nitens, Sitotroga cerealella* (Angoumois grain moth), *Sparganothis pilleriana, Spodoptera* spp. (army worm), *Spodoptera exigua* (beet armyworm), *Spodoptcra fugiperda* (fall armyworm), *Spodoptera oridania* (Southern armyworm), *Synanthedon* spp. (root borer) *Thecla basilides, Thermisia gemmatalis, Tineola bisselliella* (webbing clothes moth), *Trichoplusia ni* (cabbage looper), *Tutsabsoluta, Yponomeuta* spp., *Zeuzera coffeae* (red branch borer), *Zeuzera pyrina* (leopard moth) and *Spodoptera litura* (*fabricius*);

*mallophaga* (chewing lice): *Bovicola ovis* (sheep biting louse), *Menacanthus stramineus* (chicken body louse) and *Menopon gallinea* (common hen house);

*orthoptera* (grasshopper, locust and cricket): *Anabrus simplex* (Mormon cricket), Gryllotalpidae (mole cricket), *Locusta migratoria, Melanoplus* spp. (grasshopper), *Microcentrum retinerve* (angular winged katydid), *Pterophylla* spp. (katydid), *Chistocerca gregaria, Scudderia furcata* (fork tailed bush katydid) and *Valanga nigricorni;*

*phthiraptera* (sucking louse): *Haematopinus* spp. (cattle louse and hog louse), *Linognathus villus* (sheep louse), *Pediculus humanus* capitis (body louse), *Pediculus humanushumanus* (body louse) and *Pthirus pubis* (crab louse);

*Siphonaptera* (*daphnia*): *Ctenocephalides canis* (dog flea), *Ctenocephalides felis* (cat flea) and *Pulex irritans* (human flea);

*Thysanoptera* (*thrip*): *Frankliniella fusca* (tobacco *thrip*), *Frankliniella occidentalis* (Western flower *thrip*), *Frankliniella shultzei, Frankliniella williamsi* (corn *thrip*), *Heliothrips haemorrhaidalis* (greenhouse *thrip*), *Riphiphorothrips cruentatus, Scirtothrips* spp, *Scirtothrips* cirri (citrus *thrip*), *Scirtothrips dorsalis* (yellow tea *thrip*), *Taeniothrips rhopalantennalis* and *Thrips* spp.;

*thysanura* (bristletail): *Lepisma* spp. (silverfish) and *Thermobia* spp. (firebrats);

*Acarina* (mite and tick): *Acarapsis woodi* (tracheal mite of honeybee), *Acarus* spp. (food mite), *Acarus siro* (grain mite), *Aceria mangiferae* (mango bud mite), *Aculops* spp., *Aculops lycopersici* (tomato russet mite), *Aculopspele kasi, Aculuspele kassi, Aculus schlechtendali* (apple rust mite), *Amblyomma amcricanum* (lone star tick), *Boophilus* spp. (Tick), *Brevipalpus obovatus* (privet mite), *Brevipalpus phoenicis* (red and black flat mite), *Demodex* spp. (mange mites), *Dermacentor* spp. (hard tick), *Dermacentor variabilis* (american dog tick), *Dermatophagoides pteronyssinus* (house dust mite), *Eotetranycus* spp., *Eotetranychus carpini* (yellow spider mite), *Epitimerus* spp., *Eriophyes* spp., odes spp., (tick), *Metatetranycus* spp., *Notoedrescati, Oligonychus* spp., *Oligonychus coffee, Oligonychus ilicus* (Southern red mite), *Panonychus* spp., *Panonychus* cirri (citrus red mite), *Panonychus ulmi* (European red mite), *Phyllocoptruta oleivora* (citrus rust mite), *Polyphagotarsonemus latus* (broad mite), *Rhipicephalus sanguineus* (brown dog tick), *Rhizoglyphus* spp. (bulb mite), *Sarcoptes scabiei* (itch mite), Tegolophusperseaflorae, *Tetranychus* spp., *Tetranychus urticae* (two-spotted spider mite) and *Varroa destructor* (bee mite);

Nematoda (nematode): *Aphelenchoides* spp. (bud and leaf&pine wood nematode), *Belonolaimus* spp. (sting nematodes), *Criconemella* spp. (ring nematode), *Dirofilaria immitis* (dog heartworm), *Ditylenchus* spp. (stem and bulb nematode), *Heterodera* spp. (cyst nematode), *Heterodera zeae* (corn cystnematode), *Hirschmanniella* spp. (root nematode), *Hoplolaimus* spp. (lance nematode), *Meloidogyne* spp. (root-knot nematode), *Meloidogyne incognita* (root-knot nematode), *Onchocerca volvulus* (hook-tail worm), *Pratylenchus* spp. (lesion nematode), *Radopholus* spp. (burrowing nematode) and *Rotylenchus reniformis* (kidney-shaped nematode); and General class (general classes of insects): *Scutigerella immaculata.*

Owing to their positive properties, the compound of formula (I) may be used advantageously for protecting important crops, domestic and livestock animals of agricultural and horticultural fields, as well as the environment customary for humans, against pests and/or mites.

The amount of the compound of formula (I) used to achieve the desired effect will vary depending upon various factors, for example, the compound used, the crop to be protected, the type of the pest, the infection level, the climatic conditions, the administration method and the dosage form employed.

The ingredients of the dosage forms or compositions described herein are selected in accordance with the physical properties of the active ingredient, the route of application and environmental factors such as the soil type, moisture and temperature.

The useful dosage forms include liquid agents such as solutions (including emulsifiable concentrates), suspensions and emulsions (including microemulsions and/or suspensions) and the like, which may optionally be viscous gels. The useful dosage forms also include solids such as powders, granules, tablets, pills, films and the like, which may be water-dispersible ("wettable") or water-soluble. The effective ingredient can be microencapsulated and made into suspension or solid dosage form; in addition, the entire dosage form of the active ingredient may also be encapsulated. The capsule can control or delay the release of the effective ingredient. Sprayable dosage forms can be diluted in a suitable medium, and the spray volume used is about one to several hundred liters per hectare. The composition with high concentration is mainly used as an intermediate for further processing.

Typical solid diluents are described in Watkins et al, *Handbook of Insecticide Dust Diluents and Carriers,* 2nd Ed., Dorland Books, Caldwell, New Jersey. Typical liquid diluents are described in Marsden, *SolventsGuide,* 2nd Ed., Interscience, New York, 1950. Surfactants and recommended applications are listed in *McCutcheon's Detergents and Emulsifiers Annual*, Allued Publ. Corp., Ridgewood, New Jersey, and Sisely and Wood, *Encyclopedia of Surface Active Agents*, Chemical Publishing Co., Inc., New York, 1964. All dosage forms may contain small amounts of additives to reduce foaming, prevent caking, prevent corrosion, prevent the growth of microorganism, etc., or be added with thickeners to increase viscosity.

Surfactants include, for example, polyethoxylated alcohols, polyethoxylated alkylphenols, polyethoxylated sorbitol fatty acid esters, sulfonated dialkyl succinates, alkyl sulfates, alkyl benzene sulfonates, organosilanes, N,N-dialkyl taurates, lignosulfonates, aldehyde condensates for naphthalenesulfonates, polycarboxylates, and polyoxyethylene/polyoxypropylene block copolymers. Solid diluents include, for example, clays such as bentonite, montmorillonite, attapulgite and kaolin, starches, sugars, silica, talc, celite, urea, calcium carbonate, sodium carbonate, sodium bicarbonate and sodium sulfate; liquid diluents include, for example, water, N,N-dimethylformamide, dimethylsulfone, N-alkylpyrrolinone, ethylene glycol, polypropylene glycol, paraffin, alkylbenzene, alkylnaphthalene, olive oil, castor oil, linseed oil, tung oil, sesame oil, corn oil, peanut oil, cottonseed oil, soybean oil, rapeseed oil and cacao oil, fatty acid esters, ketones such as cyclohexanone, 2-heptanone, isophorone and 4-hydroxy-4-methyl-2-pentanone, and alcohols such as methanol, cyclohexanol, dodecanol and tetrahydrofuranol.

Solutions, including emulsifiable concentrates, can be prepared by simply mixing the components. Powders and fine powders may be prepared by mixing and typically by grinding in a hammer mill or fluid-energy mill, typically by wet milling; see, for example, U.S. Pat. No. 3,060,084, granules and pills are produced by spraying the active substance onto freshly-prepared granular carriers or by granulation techniques. See Browning, "Agglomeration", Chemical Engineering, Dec. 4, 1967, pp 147-48, Perry's Chemical Engineer's Handbook, 4th Ed., McGraw-Hill, New York, 1963, Pages 8-57 and following, and WO 91/13546. Pills are prepared by the method described in U.S. Pat. No. 4,172,714, water dispersible and water soluble granules are prepared by the methods described in U.S. Pat. Nos. 4,144,050, 3,920,442 and DE 3246493, and tablets are prepared by the methods described in U.S. Pat. Nos. 5,180,587, 5,232,701 and 5,208,030. Films may be prepared by the methods described in GB2095558 and U.S. Pat. No. 3,299,566.

More information on processing can be found in U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, Weed Control as a Science, John Wiley and Sons, Inc., New York 1961, pp 81-96; and Hance et al., Weed Control Handbook, 8th Ed., Blackwell Scientific Publications, Oxford, 1989.

Herein, for certain applications of the composition, for example, in agriculture, one, two or more of other bactericides, insecticides, acaricides, herbicides, plant growth regulators or fertilizers, etc. may be added to the insecticidal and/or acaricidal composition described herein, thereby bringing additional advantages and effects.

Beneficial Effects

The compound of formula (I) described herein exhibits good activity against a variety of pests and mites in agriculture or other fields. Moreover, these compounds can achieve a good control effect at a very low dosage, and thus can be used for the manufacturing of pesticides and/or acaricides.

Definitions and Description

Unless otherwise defined, all technical and scientific terms used herein have the same meaning as commonly understood by those skilled in the art to which the subject matter of the claims belong. Unless otherwise indicated, all patents, patent applications, and publications referred to herein are incorporated herein by reference in their entirety. If there are multiple definitions for terms herein, those in this section prevail.

It should be understood that definitions of standardized chemical terms can be found in the literature of reference (including Carey and Sundberg "ADVANCED ORGANIC CHEMISTRY $4^{TH}$ ED." Vols. A (2000) and B (2001), Plenum Press, New York). Unless otherwise indicated, conventional methods within the skill of the art are employed, such as mass spectrometry, NMR, IR and UV/Vis spectroscopy, and pharmacological methods. Unless a specific definition is set forth, the terminology used herein in the pertinent description of analytical chemistry, organic synthetic chemistry, and pharmaceutical and medicinal chemistry is known in the art. Standard techniques can be used in chemical synthesis, chemical analysis, pharmaceutical preparation, preparations and delivery, and treatment of patients. For example, the reaction and purification can be carried out using the instructions of the manufacturer for use of the kit, or in a manner known in the art or as described herein. The techniques and methods described above can generally be implemented according to conventional methods well known in the art, as described in various general and relatively specific documents referred to and discussed in this specification. In the present specification, groups and substituents thereof can be selected by those skilled in the art to provide stable moieties and compounds. When a substituent is described by a general formula written from left to right, the substituent also includes chemically-equivalent substituents that are obtained when the structural formula is written from right to left, provided that it conforms to the valence bond rule. For example, $CH_2O$ is equivalent to $OCH_2$, and may be attached to the substitution site either with an oxygen atom or with a methylene carbon atom.

The term "pharmaceutically acceptable salt" as used herein refers to a salt that retains the biological effectiveness of the free acid and free base of the specified compound and that is not biologically or otherwise undesirable. The compound of the present application also comprises a pharmaceutically acceptable salt, such as nitrate, hydrochloride, sulfate, phosphate, acetate, trifluoroacetate, malate, citrate, or the like, which may be generally used in the agricultural and horticultural fields. The pharmaceutically acceptable salt refers to the form in which the base group in the parent compound is converted into a salt. The pharmaceutically acceptable salt includes, but is not limited to, inorganic or organic acid salts of base groups such as amine (amino) groups. The pharmaceutically acceptable salt of the present application may be synthesized from the parent compound by reacting a basic group in the parent compound with 1-4 equivalents of an acid in a solvent system. Suitable salts are listed in Remingtong's Pharmaceutical Scicences, $17^{th}$ Ed., Mack Publishing Company, Easton, Pa., 1985, p. 1418 and Journal of Pharmaceutical Science, 66, 2(1977), for example, the hydrochloride. The term "stereoisomer" as used herein refers to an isomer resulting from the different arrangement of atoms in a molecule in space. The compound of formula (I) contains asymmetric or chiral centers, and therefore is present in different stereoisomeric forms. All stereo-structures and mixtures of formula (I) are as such, including racemic mixtures, as part of the present application. Diastereomeric mixtures can be separated into the individual diastereomers, based on their different physicochemical properties, by well-known means, e.g., resolution of enantiomers may be converted into diastereoisomers by reaction with an appropriate optically-active substance (e.g., a chiral alcohol or Mosher's acid chloride), and the diastereomers are separated and converted (e.g., hydrolyzed) to the corresponding single isomers. Some of the compounds of formula (I) may be atropisomers (e.g., substituted aryl) which are also part of the present application. The enantiomers may also be separated by using chiral chromatography columns. The compounds of formula (I) may be present in different tautomeric forms, all of which are encompassed by the present application, for example, including compounds in the form of keto-enol and imine-enamine.

DETAILED DESCRIPTION

The technical solutions of the present disclosure will be further illustrated in detail with reference to the following specific examples. It should be understood that the following embodiments are merely exemplary illustration and explanation of the present disclosure, and should not be construed as limiting the protection scope of the present disclosure. All techniques implemented based on the content of the present disclosure described above are encompassed within the protection scope of the present disclosure.

Unless otherwise stated, the starting materials and reagents used in the following examples are all commercially available products or can be prepared using known methods.

The LC-MS detection analysis in the following examples used the following chromatographic conditions:

Chromatographic column: Agilent ZORBAX SB-C18 150 mm×4.6 mm, 5 μm (i.d);

Detection wavelength: 254 nm; flow rate: 0.8 mL/min; column temperature: 30° C.;

Gradient elution conditions:

| Time (min) | Methanol (%) | 0.1% aqueous formic acid (volume %) |
|---|---|---|
| 0.00 | 50 | 50 |
| 5.00 | 50 | 50 |
| 15.00 | 90 | 10 |
| 20.00 | 90 | 10 |
| 25.00 | 90 | 10 |

SYNTHETIC EXAMPLES

Example 1: Preparation of N-((6-chloropyridin-3-yl)methyl)-4-(5-(3,5-dichloro-4-fluorophenyl)-5-(trifluoromethyl)-4,5-dihydroisoxazol-3-yl)-2-methylbenzamide (Compound 1)

First step of reaction: preparation of methyl (Z)-4-((hydroxyimino)methyl)-2-methylbenzoate: 17.80 g (0.1 mol) of methyl 4-formyl-2-methylbenzoate, 8.35 g (0.12 mol) of hydroxylamine hydrochloride and 12.30 g (0.15 mol) of sodium acetate were dissolved sequentially in a mixed solution of 50 mL of water and 200 mL of ethanol at room temperature. The reaction solution was stirred for 5 h. The reaction mixture was concentrated, and added with ethyl acetate and aqueous sodium hydroxide (2M) for dilution, followed by phase separation. The organic layer was washed with saturated brine and dried over anhydrous sodium sulfate, subjected to suction filtration, and dried to give the product (17.76 g, yield: 92%).

LC-MS $[M+H]^+$=194.08, $[M+Na]^+$=216.06, $[M+K]^+$=232.03.

Second step of reaction: preparation of 1,3-dichloro-2-fluoro-5-(3,3,3-trifluoroprop-1-en-2-yl)benzene: under nitrogen atmosphere, 4.18 g (0.02 mol) of (3,5-dichloro-4-fluorophenyl)boronic acid, 6.90 g (0.05 mol) of potassium carbonate, 0.35 g (0.0005 mol) of bis(triphenylphosphine) palladium(II) chloride and 80 mL of toluene were added to a three-necked flask at room temperature and stirred. To the mixture described above was added 5.25 g (0.03 mol) of 2-bromo-3,3,3-trifluoroprop-1-ene in portions. After the addition was completed, the reaction solution was stirred at 80° C. for 9 h, and cooled to room temperature. 50 mL of water was added to the reaction solution described above, followed by phase separation. The aqueous layer was extracted with toluene (30 mL×2), and the organic phases were combined, washed with saturated brine, dried over anhydrous sodium sulfate and filtered. The filtrate was concentrated under reduced pressure and subjected to column chromatography (eluent: ethyl acetate:petroleum ether (1:8)) to give the product (3.41 g, yield: 66%).

LC-MS $[M+H]^+$=258.97, $[M+Na]^+$=280.95, $[M+K]^+$=296.92.

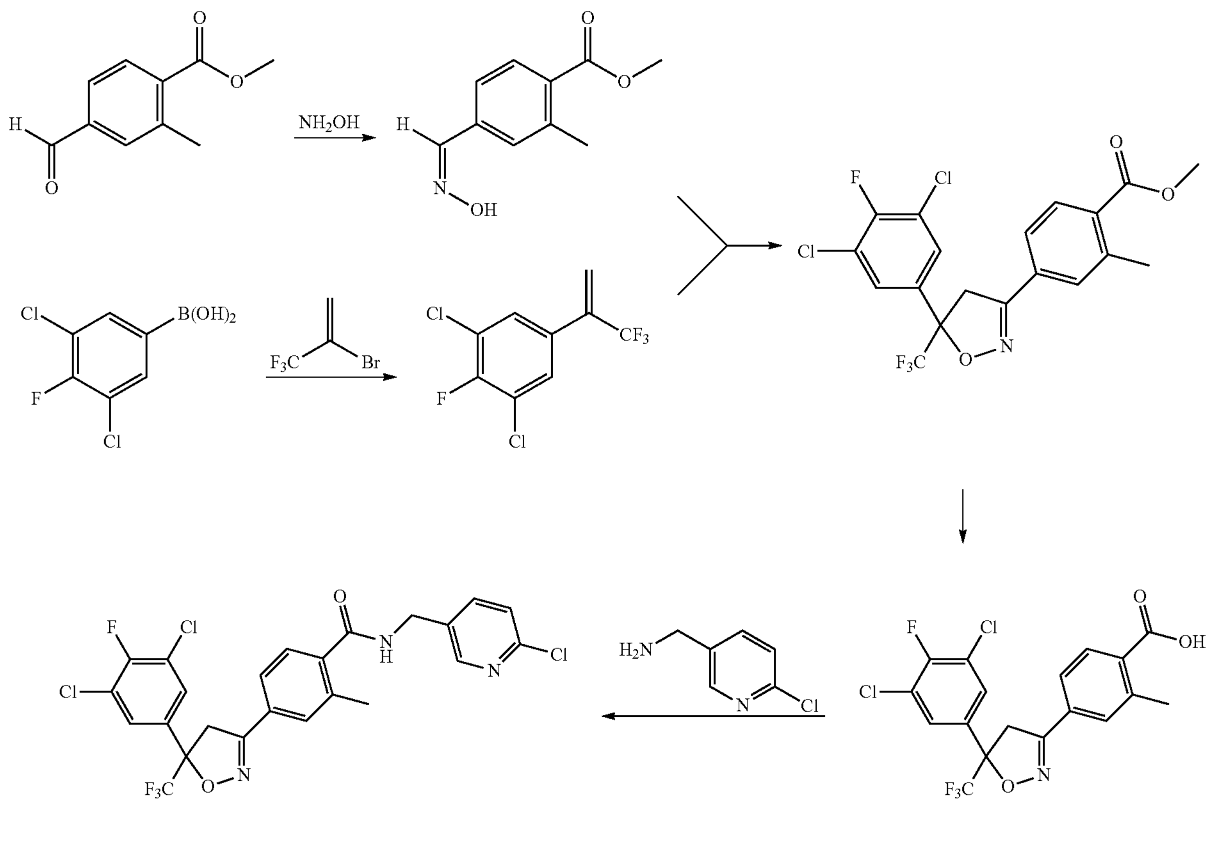

Third step of reaction: preparation of methyl 4-(5-(3,5-dichloro-4-fluorophenyl)-5-(trifluoromethyl)-4,5-dihydroisoxazol-3-yl)-2-methylbenzoate: 3.86 g (0.02 mol) of methyl (Z)-4-((hydroxyimino)methyl)-2-methylbenzoate, 4.45 g (0.033 mol) of N-chlorosuccinimide and 35 mL of N,N-dimethylformamide were added to a three-necked flask at room temperature, and the reaction solution was stirred at 40° C. for 2 h, and cooled to room temperature. A solution of 4.40 g (0.017 mol) of 1,3-dichloro-2-fluoro-5-(3,3,3-trifluoroprop-1-en-2-yl)benzene and 3.33 g (0.033 mol) of triethylamine in 20 mL of N,N-dimethylformamide was added to the mixture described above, and the reaction mixture was stirred at room temperature for 20 h, added with water and ethyl acetate for dilution, followed by phase separation. The organic phase was washed twice with water, and the aqueous phase was extracted twice with ethyl acetate. The organic phases were combined, washed with saturated brine, dried over anhydrous sodium sulfate, and filtered. The filtrate was concentrated under reduced pressure, and the residue was subjected to column chromatography (eluent: ethyl acetate:petroleum ether (1:6)) to give the product (2.52 g, yield: 33%).

LC-MS $[M+H]^+=450.03$, $[M+Na]^+=472.01$, $[M+K]^+=487.98$.

Fourth step of reaction: preparation of 4-(5-(3,5-dichloro-4-fluorophenyl)-5-(trifluoromethyl)-4,5-dihydroisoxazol-3-yl)-2-methylbenzoic acid: 2.25 g (0.005 mol) methyl 4-(5-(3,5-dichloro-4-fluorophenyl)-5-(trifluoromethyl)-4,5-dihydroisoxazol-3-yl)-2-methylbenzoate was added to 10 mL of aqueous 2N sodium hydroxide solution at room temperature, and the reaction mixture was added with 10 mL of tetrahydrofuran for dilution, stirred for 2 h, adjusted to pH=2 with 1M diluted hydrochloric acid, and subjected to suction filtration, and the filter cake was washed with water and dried to give the product (2.01 g, yield: 92%).

LC-MS $[M+H]^+=436.02$, $[M+Na]^+=458$, $[M+K]^+=473.97$.

Fifth step of reaction: preparation of N-((6-chloropyridin-3-yl)methyl)-4-(5-(3,5-dichloro-4-fluorophenyl)-5-(trifluoromethyl)-4,5-dihydroisoxazol-3-yl)-2-methylbenzamide: 1.75 g (0.004 mol) of 4-(5-(3,5-dichloro-4-fluorophenyl)-5-(trifluoromethyl)-4,5-dihydroisoxazol-3-yl)-2-methylbenzoic acid, 1.03 g (0.008 mol) of di(isopropyl)ethylamine and 2.29 g (0.0044 mol) of benzotriazol-1-yl-oxytripyrrolidinophosphonium hexafluorophosphate were dissolved sequentially in 30 mL of dichloromethane at 0° C. The reaction mixture was stirred for 2 h. To the solution described above was added 0.68 g (0.0048 mol) of (6-chloropyridin-3-yl)methylamine at room temperature. The reaction mixture was stirred at room temperature for 12 h. 20 mL of water was added to the reaction system, followed by phase separation. The aqueous phase was extracted twice with dichloromethane. The organic phases were combined, washed with saturated brine, and dried over anhydrous sodium sulfate. The organic phase was precipitated under reduced pressure and subjected to column chromatography (eluent: ethyl acetate: petroleum ether (1:3)) to give product (1.61 g, yield: 72%).

LC-MS $[M+H]^+=560.03$, $[M+Na]^+=582.01$, $[M+K]^+=597.98$.

$^1$H-NMR (400 MHz, solvent $CDCl_3$) δ (ppm): 8.42 (1H, s), 7.75 (1H, d), 7.58 (2H, d), 7.51 (2H, d), 7.42 (1H, d), 7.36 (1H, d), 6.24 (1H, s), 4.63 (2H, s), 4.07 (1H, d), 3.68 (1H, d), 2.47 (3H, s).

Example 2: Preparation of N-((6-chloropyridin-3-yl)methyl)-2-methyl-4-(5-(trifluoromethyl)-5-(3,4,5-trifluorophenyl)-4,5-dihydroisoxazol-3-yl)benzamide (Compound 2)

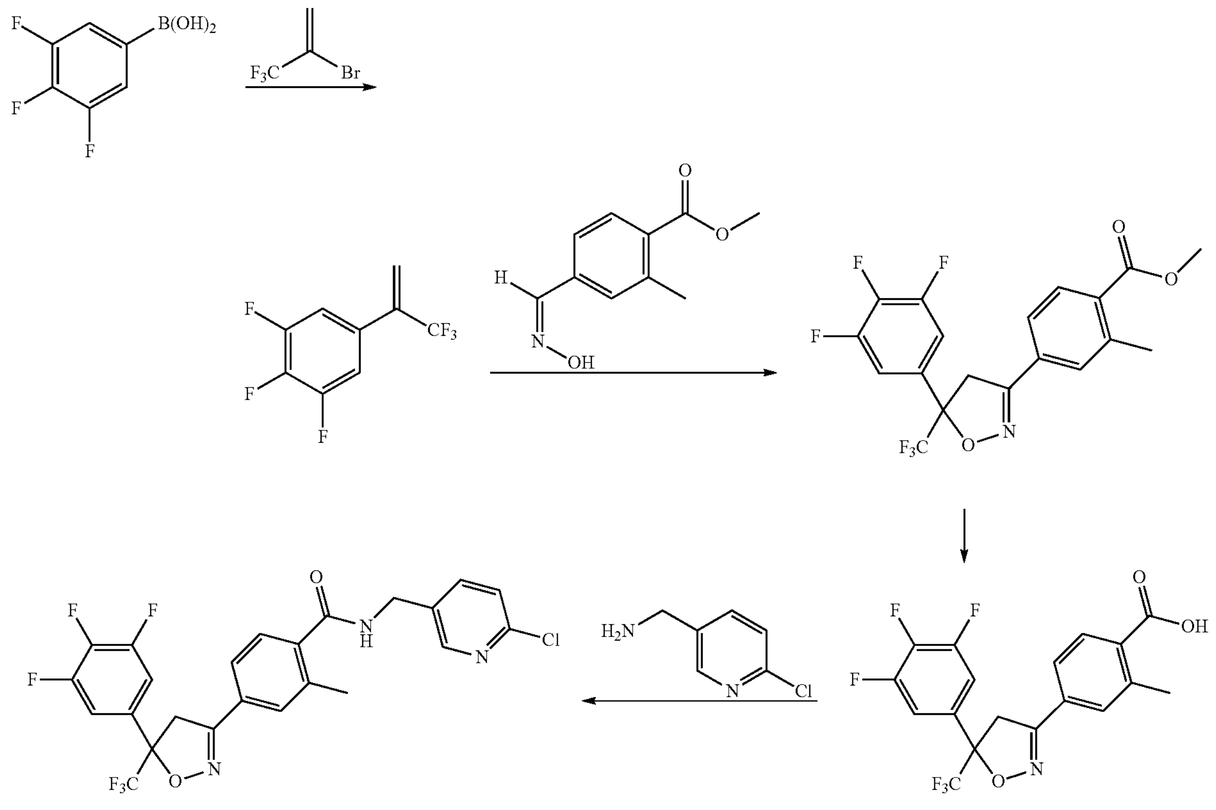

First step of reaction: preparation of 1,2,3-trifluoro-5-(3,3,3-trifluoroprop-1-en-2-yl)benzene: under nitrogen atmosphere, 3.52 g (0.02 mol) of 3,4,5-trifluorophenylboronic acid, 6.90 g (0.05 mol) of potassium carbonate, 0.35 g (0.0005 mol) of bis(triphenylphosphine)palladium(II) chloride and 80 mL of toluene were added to a three-necked flask at room temperature and stirred. To the mixture described above was added 5.25 g (0.03 mol) of 2-bromo-3,3,3-trifluoroprop-1-ene in portions. After the addition was completed, the reaction solution was stirred at 80° C. for 9 h, and cooled to room temperature. 50 mL of water was added to the reaction solution described above, followed by phase separation. The aqueous layer was extracted with toluene (30 mL×2), and the organic phases were combined, washed with saturated brine, dried over anhydrous sodium sulfate and filtered. The filtrate was concentrated under reduced pressure and subjected to column chromatography (eluent: ethyl acetate:petroleum ether (1:8)) to give the product (3.25 g, yield: 72%).

LC-MS $[M+H]^+$=227.03, $[M+Na]^+$=249.01, $[M+K]^+$=264.98.

Second step of reaction: preparation of methyl 2-methyl-4-(5-(trifluoromethyl)-5-(3,4,5-trifluorophenyl)-4,5-dihydroisoxazol-3-yl)benzoate: 3.86 g (0.02 mol) of methyl (Z)-4-((hydroxyimino)methyl)-2-methylbenzoate, 4.45 g (0.033 mol) of N-chlorosuccinimide and 35 mL of N,N-dimethylformamide were added to a three-necked flask at room temperature, and the reaction solution was stirred at 40° C. for 2 h, and cooled to room temperature. A solution of 3.84 g (0.017 mol) of 1,2,3-trichloro-5-(3,3,3-trifluoroprop-1-en-2-yl)benzene and 3.33 g (0.033 mol) of triethylamine in 20 mL of N,N-dimethylformamide was added to the mixture described above, and the reaction mixture was stirred at room temperature for 20 h, added with water and ethyl acetate for dilution, followed by phase separation. The organic phase was washed twice with water, and the aqueous phase was extracted twice with ethyl acetate. The organic phases were combined, washed with saturated brine, dried over anhydrous sodium sulfate, and filtered. The filtrate was concentrated under reduced pressure, and the residue was subjected to column chromatography (eluent: ethyl acetate: petroleum ether (1:6)) to give the product (2.69 g, yield: 38%).

LC-MS $[M+H]^+$=418.09, $[M+Na]^+$=440.07, $[M+K]^+$=456.04.

Third step of reaction: preparation of 2-methyl-4-(5-(trifluoromethyl)-5-(3,4,5-trifluorophenyl)-4,5-dihydroisoxazol-3-yl)benzoic acid: 2.09 g (0.005 mol) of methyl 2-methyl-4-(5-(trifluoromethyl)-(5-(3,4,5-trifluorophenyl)-4,5-dihydroisoxazol-3-yl)benzoate was added to 10 mL of aqueous 2N sodium hydroxide solution at room temperature, and the reaction mixture was added with 10 mL of tetrahydrofuran for dilution, stirred for 2 h, adjusted to pH=2 with 1M diluted hydrochloric acid, and subjected to suction filtration, and the filter cake was washed with water and dried to give the product (1.91 g, yield: 95%).

LC-MS $[M+H]^+$=404.07, $[M+Na]^+$=426.05, $[M+K]^+$=442.02.

Fourth step of reaction: preparation of N-((6-chloropyridin-3-yl)methyl)-2-methyl-4-(5-(trifluoromethyl)-5-(3,4,5-trifluorophenyl)-4,5-dihydroisoxazol-3-yl)benzamide: 1.61 g (0.004 mol) of 2-methyl-4-(5-(trifluoromethyl)-5-(3,4,5-trifluorophenyl)-4,5-dihydroisoxazol-3-yl)benzoic acid, 1.03 g (0.008 mol) of di(isopropyl)ethylamine and 2.29 g (0.0044 mol) of benzotriazol-1-yl-oxytripyrrolidino-phosphonium hexafluorophosphate were dissolved sequentially in 30 mL of dichloromethane at 0° C. The reaction mixture was stirred for 2 h. To the solution described above was added 0.68 g (0.0048 mol) of (6-chloropyridin-3-yl)methylamine at room temperature. The reaction mixture was stirred at room temperature for 12 h. 20 mL of water was added to the reaction system, followed by phase separation. The aqueous phase was extracted twice with dichloromethane. The organic phases were combined, washed with saturated brine, and dried over anhydrous sodium sulfate. The organic phase was precipitated under reduced pressure and subjected to column chromatography (eluent: ethyl acetate: petroleum ether (1:2)) to give product (1.58 g, yield: 75%).

LC-MS $[M+H]^+$=528.09, $[M+Na]^+$=550.07, $[M+K]^+$=566.04.

$^1$H-NMR (400 MHz, solvent $CDCl_3$) δ (ppm): 8.42 (1H, s), 7.75 (1H, d), 7.57 (2H, d), 7.46 (2H, d), 7.42 (1H, d), 7.36 (1H, d), 6.24 (1H, s), 4.63 (2H, s), 4.07 (1H, d), 3.68 (1H, d), 2.47 (3H, s).

Example 3: Preparation of N-((3-chloro-5-(trifluoromethyl)pyridin-2-yl)methyl)-4-(5-(3,5-dichloro-4-fluorophenyl)-5-(trifluoro methyl)-4,5-dihydroisoxazol-3-yl)-2-methylbenzamide (Compound 9)

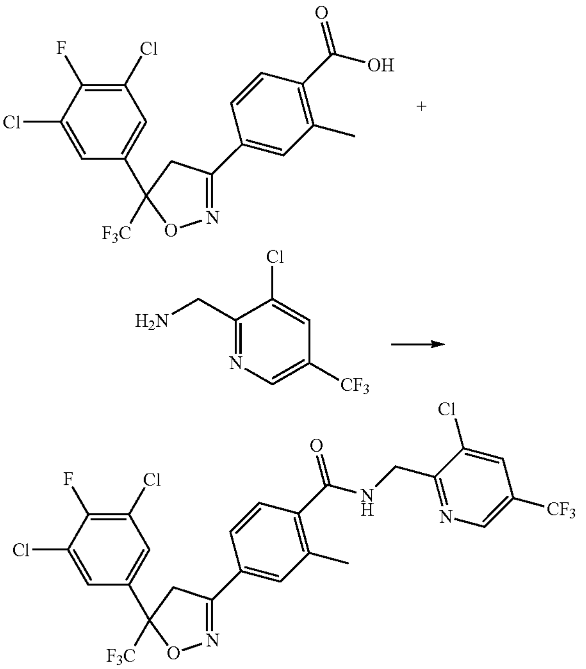

1.75 g (0.004 mol) of 4-(5-(3,5-dichloro-4-fluorophenyl)-5-(trifluoromethyl)-4,5-dihydroisoxazol-3-yl)-2-methylbenzoic acid, 1.03 g (0.008 mol) of di(isopropyl)ethylamine and 2.29 g (0.0044 mol) of benzotriazol-1-yl-oxytripyrrolidino-phosphonium hexafluorophosphate were dissolved sequentially in 30 mL of dichloromethane at 0° C. The reaction mixture was stirred for 2 h. To the solution described above was added 1.01 g (0.0048 mol) of 3-chloro-5(trifluoromethyl)pyridin-2-yl)methylamine at room temperature. The reaction solution was stirred at room temperature for 15 h. 20 mL of water was added to the reaction system, followed by phase separation. The aqueous phase was extracted twice with dichloromethane. The organic phases were combined, washed with saturated brine, and dried over anhydrous sodium sulfate. The organic phase was precipitated under reduced pressure and subjected to column chromatography (eluent: ethyl acetate:petroleum ether (1:3)) to give product (1.61 g, yield: 72%).

LC-MS $[M+H]^+=628.02$, $[M+Na]^+=650$, $[M+K]^+=665.97$.

$^1$H-NMR (400 MHz, solvent $CDCl_3$) δ (ppm): 8.22 (1H, s), 7.82 (1H, d), 7.78 (1H, d), 7.58 (2H, d), 7.51 (2H, d), 6.24 (1H, s), 4.63 (2H, s), 4.07 (1H, d), 3.68 (1H, d), 2.47 (3H, s).

Example 4: Preparation of N-((3-chloro-5-(trifluoromethyl)pyridin-2-yl)methyl)-2-methyl-4-(5-(trifluoromethyl)-5-(3,4,5-trifluorophenyl)-4,5-dihydroisoxazol-3-yl)benzamide (Compound 10)

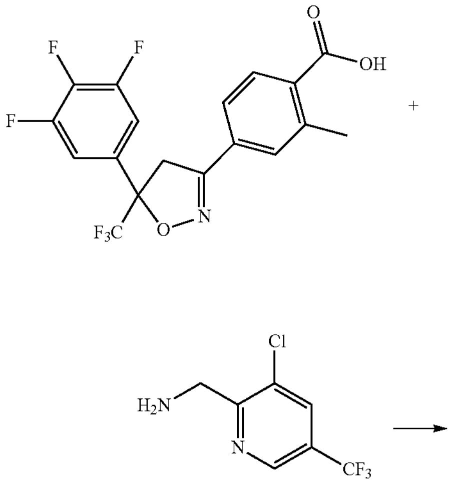

-continued

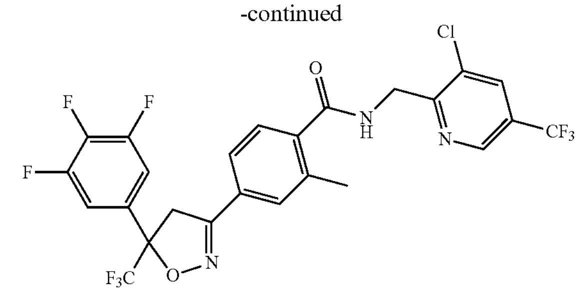

1.61 g (0.004 mol) of 2-methyl-4-(5-(trifluoromethyl)-5-(3,4,5-trifluorophenyl)-4,5-dihydroisoxazol-3-yl)benzoic acid, 1.03 g (0.008 mol) of di(isopropyl)ethylamine and 2.29 g (0.0044 mol) of benzotriazol-1-yl-oxytripyrrolidino-phosphonium hexafluorophosphate were dissolved sequentially in 30 mL of dichloromethane at 0° C. The reaction mixture was stirred for 2 h. To the solution described above was added 1.01 g (0.0048 mol) of 3-chloro-5(trifluoromethyl) pyridin-2-yl)methylamine at room temperature. The reaction solution was stirred at room temperature for 15 h. 20 mL of water was added to the reaction system, followed by phase separation. The aqueous phase was extracted twice with dichloromethane. The organic phases were combined, washed with saturated brine, and dried over anhydrous sodium sulfate. The organic phase was precipitated under reduced pressure and subjected to column chromatography (eluent: ethyl acetate:petroleum ether (1:2)) to give product (1.81 g, yield: 76%).

LC-MS $[M+H]^+=596.08$, $[M+Na]^+=618.06$, $[M+K]^+=634.03$.

$^1$H-NMR (400 MHz, solvent $CDCl_3$) δ (ppm): 8.21 (1H, s), 7.82 (1H, d), 7.76 (1H, d), 7.58 (2H, d), 7.21 (2H, d), 6.24 (1H, s), 4.63 (2H, s), 4.07 (1H, d), 3.68 (1H, d), 2.46 (3H, s).

In the present disclosure, the following compounds were also synthesized with reference to the methods in the examples described above:

TABLE 2

| Compound No. | Compound structure | LC-MS |
|---|---|---|
| 3 | 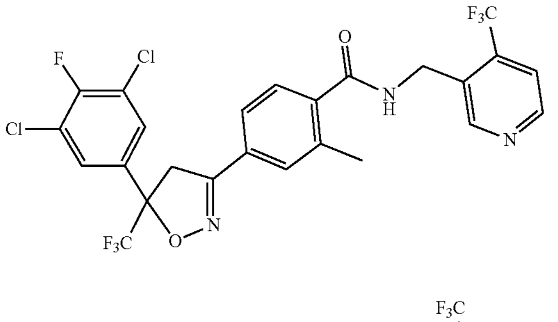 | $[M + H]^+ = 594.06$, $[M + Na]^+ = 616.04$, $[M + K]^+ = 632.01$ |
| 4 | 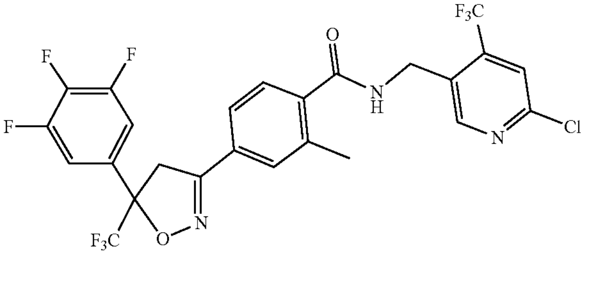 | $[M + H]^+ = 562.12$, $[M + Na]^+ = 584.1$, $[M + K]^+ = 600.07$ |

TABLE 2-continued
| Compound No. | Compound structure | LC-MS |
|---|---|---|
| 5 | 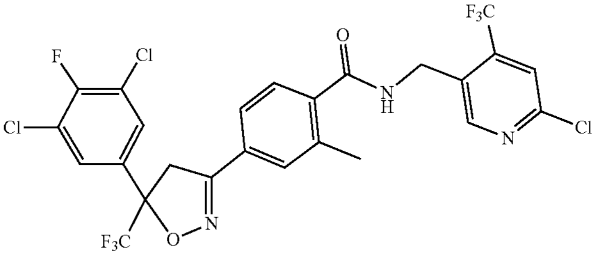 | $[M + H]^+$ = 628.02, $[M + Na]^+$ = 650, $[M + K]^+$ = 665.97 |
| 6 | 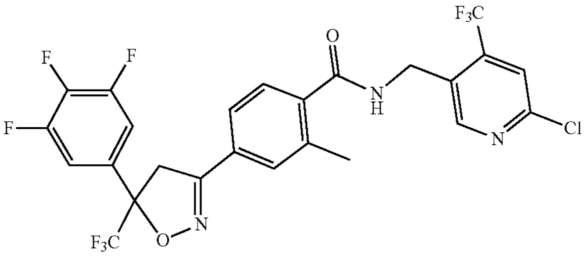 | $[M + H]^+$ = 596.08, $[M + Na]^+$ = 618.06, $[M + K]^+$ = 634.03 |
| 7 | 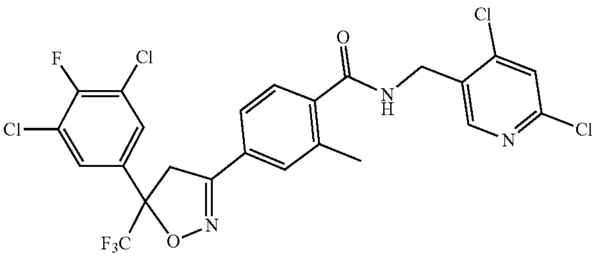 [SMILES: Cc1cc(C2=NOC(c3cc(Cl)c(F)c(Cl)c3)(C(F)(F)F)C2)ccc1C(=O)NCc1cnc(Cl)cc1Cl] | $[M + H]^+$ = 594, $[M + Na]^+$ = 615.98, $[M + K]^+$ = 631.95 |
| 8 | 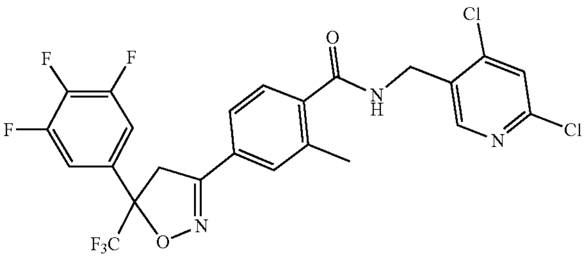 | $[M + H]^+$ = 562.05, $[M + Na]^+$ = 584.03, $[M + K]^+$ = 600 |
| 11 | 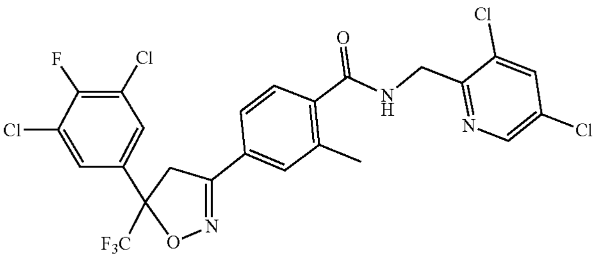 [SMILES: Cc1cc(C2=NOC(c3cc(Cl)c(F)c(Cl)c3)(C(F)(F)F)C2)ccc1C(=O)NCc1ncc(Cl)cc1Cl] | $[M + H]^+$ = 594, $[M + Na]^+$ = 615.98, $[M + K]^+$ = 631.95 |
| 12 | 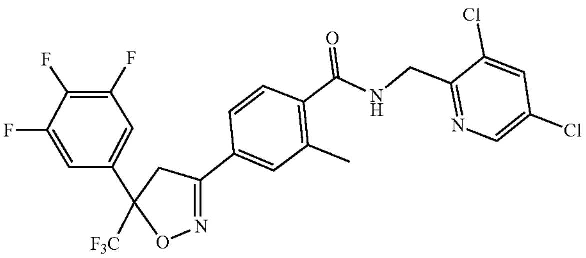 [SMILES: Cc1cc(C2=NOC(c3cc(F)c(F)c(F)c3)(C(F)(F)F)C2)ccc1C(=O)NCc1ncc(Cl)cc1Cl] | $[M + H]^+$ = 562.05, $[M + Na]^+$ = 584.03, $[M + K]^+$ = 600 |

TABLE 2-continued
| Compound No. | Compound structure | LC-MS |
|---|---|---|
| 13 | 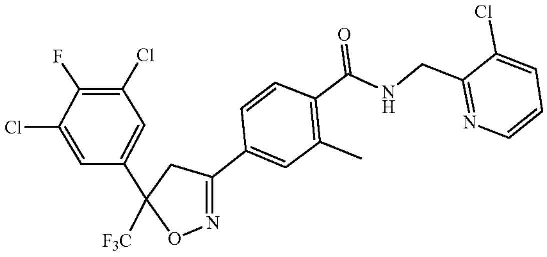 [SMILES: Cc1cc(C2=NOC(c3cc(Cl)c(F)c(Cl)c3)(C(F)(F)F)C2)ccc1C(=O)NCc1ncccc1Cl] | $[M + H]^+$ = 560.03, $[M + Na]^+$ = 582.01, $[M + K]^+$ = 597.98 |
| 14 | 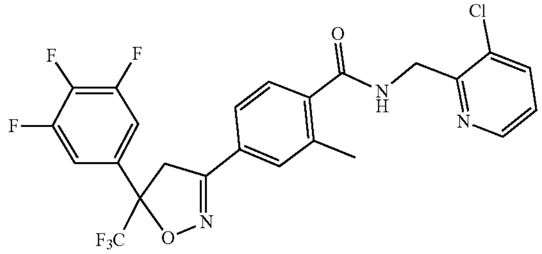 [SMILES: Cc1cc(C2=NOC(c3cc(F)c(F)c(F)c3)(C(F)(F)F)C2)ccc1C(=O)NCc1ncccc1Cl] | $[M + H]^+$ = 528.09, $[M + Na]^+$ = 550.07, $[M + K]^+$ = 566.04 |
| 15 | 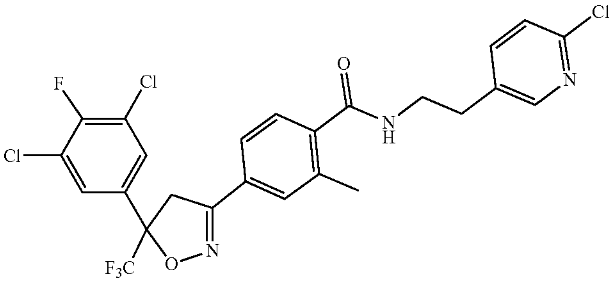 [SMILES: Cc1cc(C2=NOC(c3cc(Cl)c(F)c(Cl)c3)(C(F)(F)F)C2)ccc1C(=O)NCCc1ccc(Cl)nc1] | $[M + H]^+$ = 574.05, $[M + Na]^+$ = 596.03, $[M + K]^+$ = 612 |
| 16 | 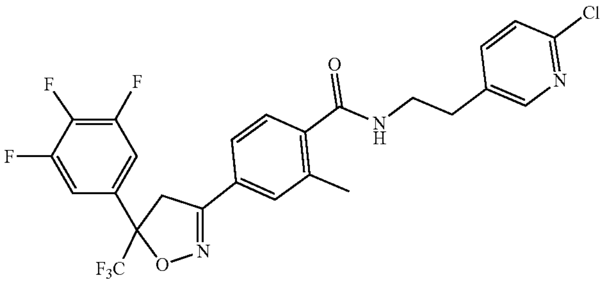 [SMILES: Cc1cc(C2=NOC(c3cc(F)c(F)c(F)c3)(C(F)(F)F)C2)ccc1C(=O)NCCc1ccc(Cl)nc1] | $[M + H]^+$ = 542.11, $[M + Na]^+$ = 564.09, $[M + K]^+$ = 580.06 |
| 17 | 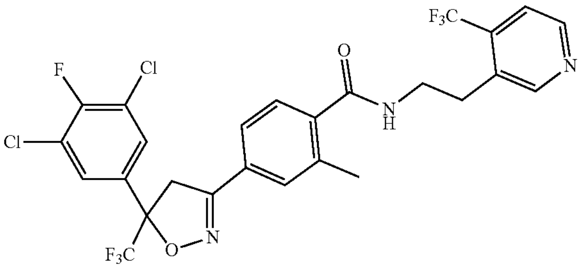 [SMILES: Cc1cc(C2=NOC(c3cc(Cl)c(F)c(Cl)c3)(C(F)(F)F)C2)ccc1C(=O)NCCc1cnccc1C(F)(F)F] | $[M + H]^+$ = 608.08, $[M + Na]^+$ = 630.06, $[M + K]^+$ = 646.03 |
| 18 | 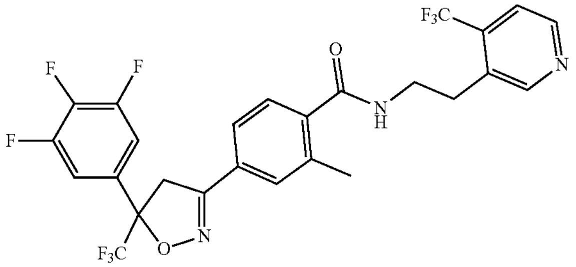 [SMILES: Cc1cc(C2=NOC(c3cc(F)c(F)c(F)c3)(C(F)(F)F)C2)ccc1C(=O)NCCc1cnccc1C(F)(F)F] | $[M + H]^+$ = 576.14, $[M + Na]^+$ = 598.12, $[M + K]^+$ = 614.09 |

TABLE 2-continued

| Compound No. | Compound structure | LC-MS |
|---|---|---|
| 19 | 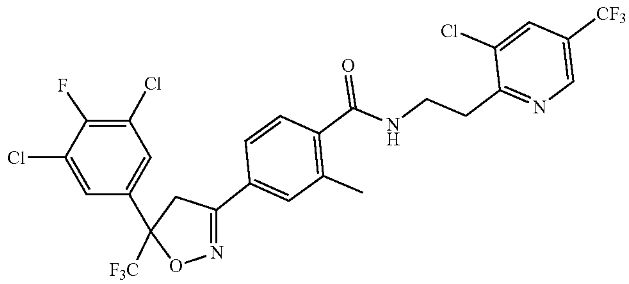 [SMILES: Cc1cc(C2=NOC(c3cc(Cl)c(F)c(Cl)c3)(C(F)(F)F)C2)ccc1C(=O)NCCc1ncc(C(F)(F)F)cc1Cl] | $[M + H]^+ = 642.04$, $[M + Na]^+ = 664.02$, $[M + K]^+ = 679.99$ |
| 20 | 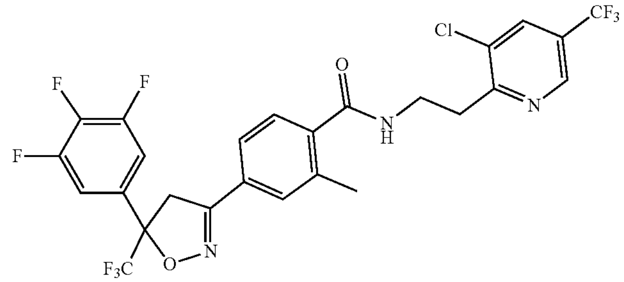 [SMILES: Cc1cc(C2=NOC(c3cc(F)c(F)c(F)c3)(C(F)(F)F)C2)ccc1C(=O)NCCc1ncc(C(F)(F)F)cc1Cl] | $[M + H]^+ = 610.1$, $[M + Na]^+ = 632.08$, $[M + K]^+ = 648.05$ |

PREPARATION EXAMPLE

In the following examples, all percentages were by weight and all dosage forms were prepared by conventional methods.

Example 5

In this example, the compound obtained in the example described above was used to prepare a wettable powder, which was specifically prepared from the starting materials of the following ratios:

Compound 1, 50.0%; dodecylphenol polyethoxy glycol ether, 4.0%; sodium lignosulfonate, 6.0%; sodium aluminosilicate, 8.0%; and montmorillonite (calcined), 32.0%.

Example 6

In this example, the compound obtained in the example described above was used to prepare a granule, which was specifically prepared from the starting materials of the following ratios:

Compound 2, 20.0%; and the other components were as follows: sodium dodecyl sulfate, 2.0%; calcium lignosulfonate, 6.0%; potassium chloride, 10.0%; polydimethylsiloxane, 1.0%; and soluble starch making up the rest.

Example 7

In this example, the compound obtained in the example described above was used to prepare an extruded pill, which was specifically prepared from the starting materials of the following ratios:

Compound 3, 30.0%; anhydrous calcium sulfate, 9.0%; crude calcium lignosulfonate, 4.0%; sodium alkyl naphthalene sulfonate, 1.0%; and calcium/magnesium bentonite, 56.0%.

Example 8

In this example, the compound obtained in the above examples was used to prepare an emulsifiable concentrate, which was specifically prepared from the starting materials of the following ratios:

Compound 9, 25.0%; solvent 150, 60%; PEG 400, 5%; Rhodacal 70/B, 3%; and Rhodameen RAM/7, 7%.

Example 9

In this example, the compound obtained in the above example was used to prepare an aqueous suspension, which was specifically prepared from the starting materials of the following ratios:

Compound 10, 30.0%; POE polystyrene phenyl ether sulfate, 5.0%; xanthan gum, 0.5%; polyethylene glycol, 5%; triethanolamine, 1%; sorbitol, 0.5%; and water making up the rest.

Assay for Biological Activity

Example 10

1. Determination of Insecticidal Activity

In this example, the compounds prepared in the above examples were used to test the insecticidal activity of several insects.

For determination of insecticidal activity, the test method was as follows: a test solution with a desired concentration was prepared by dissolving a test compound sample in a suitable solvent (the kind of solvent was such as acetone, methanol, DMSO, etc., and was selected according to its dissolving ability for the sample). The test cell was composed of a small open container with 12-15 day old radish plants inside. The plants were pre-infested by placing 30-40 pests located on one leaf cut from the cultivated plant on one leaf of the test plant (leaf cutting method). As the leaves dehydrated, the pests moved on the test plants. After the pre-infesting, the soil of the test cells was covered with a layer of sand.

The test method was as follows: the test was repeated for three times, and after spraying the formulated test compound, each test unit was allowed to dry for 1 hour, and then a black mesh cover was placed at the top. The test units were kept in a growth chamber at 25° C. and 70% relative humidity for 6 days. The mortality (fatality rate) of the insects was then visually assessed for each test unit, and the fatality rate was calculated as follows:

$$\text{Fatality rate (\%)} = \frac{\text{Number of dead insects}}{\text{Total number of treated insects}} \times 100\%.$$

(1) Test Results for the Control of *Frankliniella occidentalis* by Exemplary Example Compounds At a dose of 25 ppm, the compounds with the fatality rate of over 80% on *Frankliniella occidentalis* were as follows: 1, 2, 3, 4, 5, 6, 7, 8, 9, 10, 11, 12, 13, 14, 15, 16, 17, 18, 19 and 20;

At a dose of 10 ppm, the compounds with the fatality rate of over 80% on *Frankliniella occidentalis* were as follows: 1, 2, 3, 4, 5, 6, 7, 8, 9, 10, 11, 12, 13, 14, 15, 16, 17, 18, 19 and 20;

At a dose of 1 ppm, the compounds with the fatality rate of over 80% on *Frankliniella occidentalis* were as follows: 1, 2, 3, 4, 5, 6, 7, 8, 9, 10, 11, 12, 13, 14, 15, 16, 17, 18, 19 and 20.

(2) Test Results for the Control of *Plutella xylostella* by Exemplary Example Compounds At a dose of 10 ppm, the compounds with the fatality rate of over 80% on *Plutella xylostella* were as follows: 1, 2, 3, 4, 5, 6, 7, 8, 9, 10, 11, 12, 13, 14, 15, 16, 17, 18, 19 and 20;

At a dose of 1 ppm, the compounds with the fatality rate of over 80% on *Plutella xylostella* were as follows: 1, 2, 3, 4, 5, 6, 7, 8, 9, 10, 11, 12, 13, 14, 15, 16, 17, 18, 19 and 20;

At a dose of 0.1 ppm, the compounds with the fatality rate of over 80% on *Plutella xylostella* were as follows: 1, 2, 3, 4, 5, 6, 7, 8, 9, 10, 11, 12, 13, 14, 15, 16, 17, 18, 19 and 20.

(3) Test Results for the Control of *Pieris rapae* by Exemplary Example Compounds At a dose of 10 ppm, the compounds with the fatality rate of over 80% on *Pieris rapae* were as follows: 1, 2, 3, 4, 5, 6, 7, 8, 9, 10, 11, 12, 13, 14, 15, 16, 17, 18, 19 and 20;

At a dose of 1 ppm, the compounds with the fatality rate of over 80% on *Pieris rapae* were as follows: 1, 2, 3, 4, 5, 6, 7, 8, 9, 10, 11, 12, 13, 14, 15, 16, 17, 18, 19 and 20;

At a dose of 0.1 ppm, the compounds with the fatality rate of over 80% on *Pieris rapae* were as follows: 1, 2, 3, 4, 5, 6, 7, 8, 9, 10, 11, 12, 13, 14, 15, 16, 17, 18, 19 and 20.

(4) Test Results for the Control of *Mythimna separata* by Exemplary Example Compounds At a dose of 10 ppm, the compounds with the fatality rate of over 80% on *Mythimna separata* were as follows: 1, 2, 3, 4, 5, 6, 7, 8, 9, 10, 11, 12, 13, 14, 15, 16, 17, 18, 19 and 20;

At a dose of 1 ppm, the compounds with the fatality rate of over 80% on *Mythimna separata* were as follows: 1, 2, 3, 4, 5, 6, 7, 8, 9, 10, 11, 12, 13, 14, 15, 16, 17, 18, 19 and 20;

At a dose of 0.1 ppm, the compounds with the fatality rate of over 80% on *Mythimna separata* were as follows: 1, 2, 3, 4, 5, 6, 7, 8, 9, 10, 11, 12, 13, 14, 15, 16, 17, 18, 19 and 20.

(5) Test Results for the Control of *Spodoptera litura* by Exemplary Example Compounds At a dose of 10 ppm, the compounds with the fatality rate of over 80% on *Spodoptera litura* were as follows: 1, 2, 3, 4, 5, 6, 7, 8, 9, 10, 11, 12, 13, 14, 15, 16, 17, 18, 19 and 20;

At a dose of 1 ppm, the compounds with the fatality rate of over 80% on *Spodoptera litura* were as follows: 1, 2, 3, 4, 5, 6, 7, 8, 9, 10, 11, 12, 13, 14, 15, 16, 17, 18, 19 and 20;

At a dose of 0.1 ppm, the compounds with the fatality rate of over 80% on *Spodoptera litura* were as follows: 1, 2, 3, 4, 5, 6, 7, 8, 9, 10, 11, 12, 13, 14, 15, 16, 17, 18, 19 and 20.

(6) Test Results for the Control of *Chilo suppressalis* by Exemplary Example Compounds At a dose of 10 ppm, the compounds with the fatality rate of over 80% on *Chilo suppressalis* were as follows: 1, 2, 3, 4, 5, 6, 7, 8, 9, 10, 11, 12, 13, 14, 15, 16, 17, 18, 19 and 20;

At a dose of 1 ppm, the compounds with the fatality rate of over 80% on *Chilo suppressalis* were as follows: 1, 2, 3, 4, 5, 6, 7, 8, 9, 10, 11, 12, 13, 14, 15, 16, 17, 18, 19 and 20;

At a dose of 0.1 ppm, the compounds with the fatality rate of over 80% on *Chilo suppressalis* were as follows: 1, 2, 3, 4, 5, 6, 7, 8, 9, 10, 11, 12, 13, 14, 15, 16, 17, 18, 19 and 20.

(7) Test Results for the Control of *Cnaphalocrocis medinalis* by Exemplary Example Compounds At a dose of 10 ppm, the compounds with the fatality rate of over 80% on *Cnaphalocrocis medinalis* were as follows: 1, 2, 3, 4, 5, 6, 7, 8, 9, 10, 11, 12, 13, 14, 15, 16, 17, 18, 19 and 20;

At a dose of 1 ppm, the compounds with the fatality rate of over 80% on *Cnaphalocrocis medinalis* were as follows: 1, 2, 3, 4, 5, 6, 7, 8, 9, 10, 11, 12, 13, 14, 15, 16, 17, 18, 19 and 20;

At a dose of 0.1 ppm, the compounds with the fatality rate of over 80% on *Cnaphalocrocis medinalis* were as follows: 1, 2, 3, 4, 5, 6, 7, 8, 9, 10, 11, 12, 13, 14, 15, 16, 17, 18, 19 and 20.

2. Determination of Acaricidal Activity

In this example, the compounds prepared in the above examples were used to test the acaricidal activity of several mite pests.

The test method was as follows: a test solution with a desired concentration was prepared by dissolving a test compound sample in a suitable solvent (the kind of solvent was such as acetone, methanol, DMSO, etc., and was selected according to its dissolving ability for the sample). A double-sided adhesive tape was cut into 2-3 cm long pieces, the pieces were attached to one end of a microscope slide, paper pieces on the adhesive tape were removed using tweezers, female adult mites which were consistent in size, bright in body color and lively in action were selected using a zero-size brush pen, the backs of the female adult mites were adhered to the double-sided adhesive tape (note: the adhesion should not cover mite feet, mite whiskers and mouthparts), with 4 rows of mites adhered to each piece and 10 heads of the mites adhered to each row.

The test method was as follows: the test was repeated for three times, and after being placed in a biochemical incubator at the temperature of (25+1) ° C. and with the relative humidity of about 85% for 4 hours, dead or inactive individuals were removed after observing through binoculars. One end of the glass slide with the mites was immersed into a drug liquid, with slightly shaking for 5 seconds, and then the slide was taken out. The excess drug liquid around the mite body and is surroundings is quickly sucked off using absorbent paper. The slide was placed in the biochemical incubator described above, and the results were checked by using binoculars after 24 hours. The mites were slightly touched by using a brush pen, the mites with immobility in feet were considered to be dead, and the fatality rate was calculated. The fatality rate was calculated as follows:

$$\text{Fatality rate (\%)} = \frac{\text{Number of dead mites}}{\text{Total number of treated mites}} \times 100\%.$$

The determination results for *Tetranychus cinnabarinus* were as follows:

At a dose of 25 ppm, the compounds with the fatality rate of over 80% on *Tetranychus cinnabarinus* were as follows: 1, 2, 3, 4, 5, 6, 7, 8, 9, 10, 11, 12, 13, 14, 15, 16, 17, 18, 19 and 20;

At a dose of 10 ppm, the compounds with the fatality rate of over 80% on *Tetranychus cinnabarinus* were as follows: 1, 2, 3, 4, 5, 6, 7, 8, 9, 10, 11, 12, 13, 14, 15, 16, 17, 18, 19 and 20;

At a dose of 1 ppm, the compounds with the fatality rate of over 80% on *Tetranychus cinnabarinus* were as follows: 1, 2, 3, 4, 5, 6, 7, 8, 9, 10, 11, 12, 13, 14, 15, 16, 17, 18, 19 and 20.

3. Test Results for Exemplary Example Compounds and Control Agents

In this example, the activity of the exemplary example compounds was compared with that of the control agent (Compound $CK_1$, number 5-241 of Patent Document WO2005085216, prepared according to the method reported in the literature). The test results are shown in Table 3 below.

$CK_1$

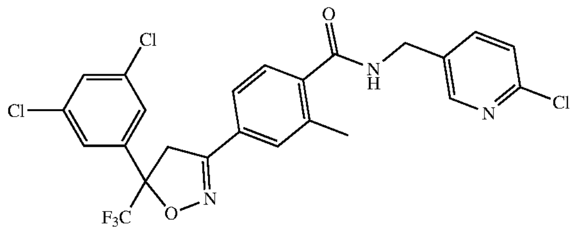

TABLE 3

| Compound | Fatality rate on *Mythimna separata* (%) 10 ppm | 1 ppm | 0.1 ppm | Fatality rate on *Chilo suppressalis* (%) 10 ppm | 1 ppm | 0.1 ppm | Fatality rate on *Plutella xylostella* (%) 10 ppm | 1 ppm | 0.1 ppm | Fatality rate on *Frankliniella occidentalis* (%) 25 ppm | 10 ppm | 1 ppm |
|---|---|---|---|---|---|---|---|---|---|---|---|---|
| 1 | 100 | 100 | 95 | 100 | 100 | 90 | 100 | 100 | 100 | 100 | 100 | 95 |
| 2 | 100 | 100 | 85 | 100 | 100 | 80 | 100 | 100 | 85 | 100 | 100 | 90 |
| 9 | 100 | 100 | 100 | 100 | 100 | 95 | 100 | 100 | 100 | 100 | 100 | 95 |
| 10 | 100 | 100 | 85 | 100 | 100 | 85 | 100 | 100 | 90 | 100 | 100 | 85 |
| $CK_1$ | 100 | 80 | 10 | 100 | 50 | 0 | 100 | 80 | 15 | 80 | 40 | 0 |

In addition to the compounds listed in the above table, other exemplary example compounds of the present disclosure have better control activity on pests and mites than the control agent. Therefore, the compound of formula (I) shows good activity against various pests and mites in the agricultural field.

The embodiments of the present disclosure have been described above. However, the present disclosure is not limited to the embodiments described above. Any modification, equivalent, improvement and the like made without departing from the spirit and principle of the present disclosure shall fall within the protection scope of the present disclosure.

The invention claimed is:

1. A compound of formula (I), or a stereoisomer, a racemate, a tautomer, a nitrogen oxide, or a pharmaceutically acceptable salt thereof, (I)

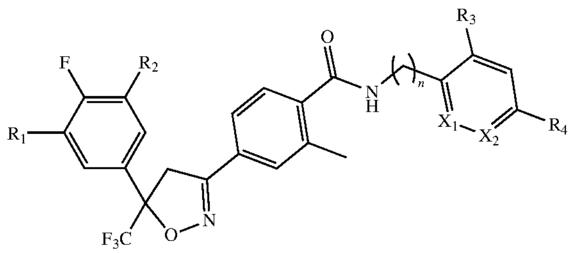

wherein $R_1$ and $R_2$ are identical or different and are each independently selected from F and Cl;

$R_3$ and $R_4$ are identical or different and are each independently selected from H, Cl and $CF_3$, and $R_3$ and $R_4$ are not simultaneously H;

$X_1$ and $X_2$ are each independently selected from CH and N, and $X_1$ and $X_2$ are not simultaneously CH or simultaneously N; and n is selected from 1 and 2.

2. The compound according to claim 1, wherein, in formula (I), $X_1$ is CH, and $X_2$ is N;

$R_1$ and $R_2$ are identical or different and are each independently selected from F and Cl;

$R_3$ and $R_4$ are identical or different and are each independently selected from H, Cl and $CF_3$, and $R_3$ and $R_4$ are not simultaneously H; and n is selected from 1 and 2.

3. The compound according to claim 1, wherein, in formula (I), $X_1$ is N, and $X_2$ is CH;

$R_1$ and $R_2$ are identical or different and are each independently selected from F and Cl;

$R_3$ and $R_4$ are identical or different and are each independently selected from Cl and $CF_3$; and n is selected from 1 and 2.

4. The compound according to claim 1, wherein the compound of formula (I) is selected from compounds 1 to 20 having substitute groups defined below:

| Compound Number | $X_1$ | $X_2$ | $R_1$ | $R_2$ | $R_3$ | $R_4$ | n |
|---|---|---|---|---|---|---|---|
| 1 | CH | N | Cl | Cl | H | Cl | 1 |
| 2 | CH | N | F | F | H | Cl | 1 |
| 3 | CH | N | Cl | Cl | $CF_3$ | H | 1 |
| 4 | CH | N | F | F | $CF_3$ | H | 1 |
| 5 | CH | N | Cl | Cl | $CF_3$ | Cl | 1 |
| 6 | CH | N | F | F | $CF_3$ | Cl | 1 |
| 7 | CH | N | Cl | Cl | Cl | Cl | 1 |
| 8 | CH | N | F | F | Cl | Cl | 1 |
| 9 | N | CH | Cl | Cl | Cl | $CF_3$ | 1 |
| 10 | N | CH | F | F | Cl | $CF_3$ | 1 |
| 11 | N | CH | Cl | Cl | Cl | Cl | 1 |
| 12 | N | CH | F | F | Cl | Cl | 1 |
| 13 | N | CH | Cl | Cl | Cl | H | 1 |
| 14 | N | CH | F | F | Cl | H | 1 |
| 15 | CH | N | Cl | Cl | H | Cl | 2 |
| 16 | CH | N | F | F | H | Cl | 2 |
| 17 | CH | N | Cl | Cl | $CF_3$ | H | 2 |
| 18 | CH | N | F | F | $CF_3$ | H | 2 |
| 19 | N | CH | Cl | Cl | Cl | $CF_3$ | 2 |
| 20 | N | CH | F | F | Cl | $CF_3$ | 2. |

5. A preparation method for the compound according to claim 1, comprising the following step A) or step B), wherein step A) comprises subjecting a compound of formula (II) and a compound of formula (III) to a condensation reaction to give the compound of formula (I);

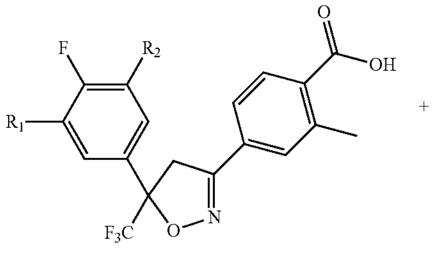

(II)

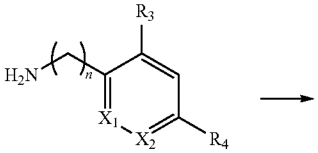

(III)

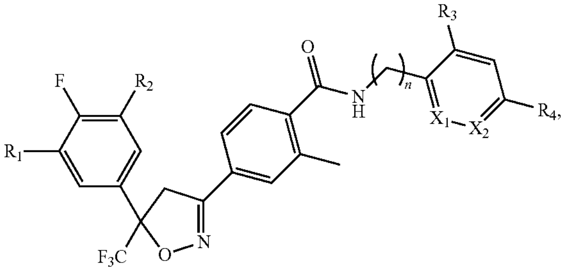

(I)

or wherein step B) comprises

B1), reacting the compound of formula (II) with a halogenating agent to give a compound of formula (IV); and B2), reacting the compound of formula (IV) with the compound of formula (III) to give the compound of formula (I);

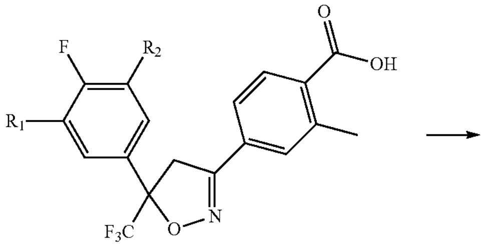

(II)

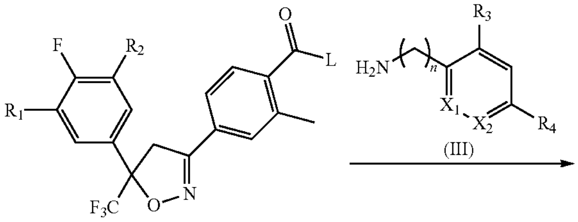

(IV)

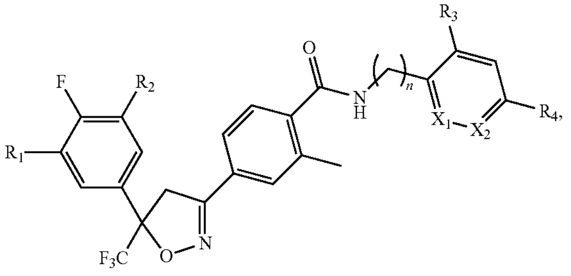

(I)

wherein $R_1$, $R_2$, $R_3$, $R_4$, $X_1$, $X_2$ and n are defined as in claim 1; and L is selected from a leaving group.

6. The preparation method according to claim 5, wherein a preparation method for the compound of formula (II) comprises:

reacting a compound of formula (VIII) with hydroxylamine or hydroxylamine hydrochloride to give a compound of formula (VI);

reacting a compound of formula (IX) with a compound of formula (X) to give a compound of formula (VII);

reacting the compound of formula (VI) with the compound of formula (VII) to give a compound of formula (V); and hydrolyzing the compound of formula (V) to give the compound of formula (II),

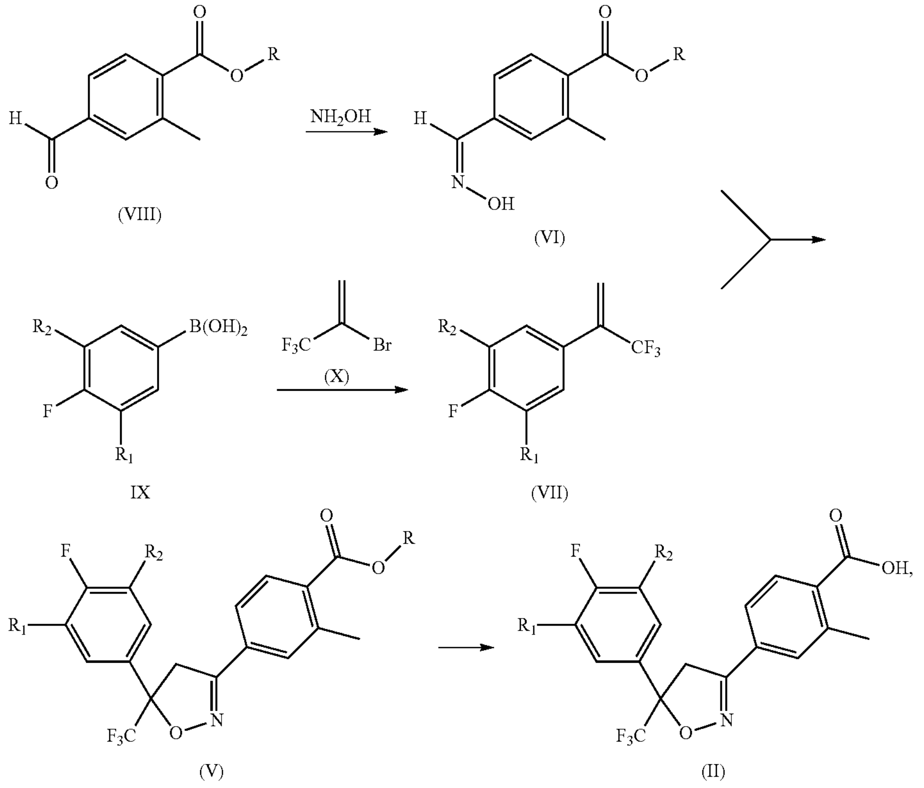

wherein R is an alkyl group containing 1 to 6 carbon atoms.

7. A pesticidal composition, comprising one, two or more of the compounds of formula (I), or the stereoisomer, the racemate, the tautomer, the nitrogen oxide or the pharmaceutically acceptable salt thereof according to claim 1 as an active ingredient.

8. A method for controlling pests and/or mites, comprising applying an effective amount of one, two or more of the compound of formula (I), or the stereoisomer, the racemate, the tautomer, the nitrogen oxide or the pharmaceutically acceptable salt thereof according to claim 1 to a growth medium of pests and/or mites.

9. A method for controlling pests and/or mites, comprising applying a pesticidal composition of claim 7 to a growth medium of pests and/or mites.

10. The pesticidal composition according to claim 7, wherein the pesticidal composition is an insecticidal or acaricidal composition.

* * * * *